United States Patent
Kaminski et al.

(10) Patent No.: US 12,421,189 B2
(45) Date of Patent: Sep. 23, 2025

(54) MODIFIED AMINO ACID DERIVATIVES FOR THE TREATMENT OF NEUROLOGICAL DISEASES AND SELECTED PSYCHIATRIC DISORDERS

(71) Applicants: UNIWERSYTET JAGIELLONSKI, Cracow (PL); WARSZAWSKI UNIWERSYTET MEDYCZNY, Warsaw (PL)

(72) Inventors: Krzysztof Kaminski, Cracow (PL); Michal Abram, Cracow (PL); Marcin Jakubiec, Wilkowice (PL); Anna Rapacz, Cracow (PL); Szczepan Mogilski, Labowa (PL); Gniewomir Latacz, Wolbrom (PL); Marta Struga, Milanowek (PL)

(73) Assignees: UNIWERSYTET JAGIELLONSKI, Cracow (PL); WARSZAWSKI UNIWERSYTET MEDYCZNY, Warsaw (PL)

( * ) Notice: Subject to any disclaimer, the term of this patent is extended or adjusted under 35 U.S.C. 154(b) by 832 days.

(21) Appl. No.: 17/593,974

(22) PCT Filed: Apr. 16, 2020

(86) PCT No.: PCT/PL2020/050028
§ 371 (c)(1),
(2) Date: Sep. 29, 2021

(87) PCT Pub. No.: WO2020/214043
PCT Pub. Date: Oct. 22, 2020

(65) Prior Publication Data
US 2022/0153694 A1     May 19, 2022

(30) Foreign Application Priority Data
Apr. 16, 2019   (PL) .......................... 429656

(51) Int. Cl.
*C07D 207/27*     (2006.01)
*A61P 25/28*      (2006.01)
*C07D 207/404*    (2006.01)
*C07D 207/416*    (2006.01)

(52) U.S. Cl.
CPC ............ *C07D 207/27* (2013.01); *A61P 25/28* (2018.01); *C07D 207/404* (2013.01); *C07D 207/416* (2013.01)

(58) Field of Classification Search
CPC ... A61P 25/28; C07D 207/27; C07D 207/404; C07D 207/416
See application file for complete search history.

(56) References Cited

U.S. PATENT DOCUMENTS

2023/0192608 A1   6/2023   Kaminski et al.
2025/0026717 A1   1/2025   Kaminski et al.

FOREIGN PATENT DOCUMENTS

WO    2020214043 A1   10/2020

OTHER PUBLICATIONS

Schmidt (Current Neurology and Neuroscience Reports (2016) 16: 95. p. 1-5) (Year: 2016).*
Kaminski (Bioorganic Medical Chemistry. 23 (2015) 2548-2561) (Year: 2015).*
Rapacz et al. (2017) "Analgesic, 1-7 antiallodynic, and anticonvulsant activity of novel hybrid molecules derived from N-benzyl-2—(2,5-dioxopyrrolidin-1-yl)propanamide and 2-(2,5-dioxopyrrolidin-1-yl)butanamide in animal models of pain and epilepsy", Naunyn-Schmiedeberg's Archives of Pharmacology, Springer, DE, vol. 390, No. 6, pp. 567-579.
Barton et al., (2001) "Pharmacological Characterization of the 6 Hz Psychomotor Seizure Model of Partial Epilepsy", Epilepsy research, 47(3):217-227.
Beirith et al., (1998) "Spinal and Supraspinal Antinociceptive Action of Dipyrone in Formalin, Capsaicin and Glutamate Tests. Study of the Mechanism of Action", European Journal of Pharmacology, 345(3):233-245.
Berge et al., (Jan. 1977) "Pharmaceutical Salts", Journal of Pharmaceutical Sciences, 66(1):1-19.
Castel-Branco et al., (2009) "The Maximal Electroshock Seizure (Mes) Model in the Preclinical Assessment of Potential New Antiepileptic Drugs", Methods and findings in experimental and clinical pharmacology, 31(2):101-106.
Dunham et al., (1957) "The Pharmacological Activity of a Series of Basic Esters of Mono- and Dialkylmalonic Acids", Journal of the American Pharmaceutical Association, 46(1):64-66.

(Continued)

*Primary Examiner* — Kortney L. Klinkel
*Assistant Examiner* — Richard Grant Peckham
(74) *Attorney, Agent, or Firm* — Mintz Levin Cohn Ferris Glovsky and Popeo, P.C.

(57) ABSTRACT

2-(2,5-dioxopyrrolidin-1-yl)propanamide and 2-(2-oxopyrrolidin-1-yl)propanamide derivatives with R-configuration at the stereogenic center are disclosed, showing broad-spectrum protective activity in animal models of epileptic seizures, pain, depression and anxiety that are simultaneously devoid of undesirable sedative effects. Additionally, the disclosed derivatives have neuroprotective effects in the in vitro and in vivo studies.

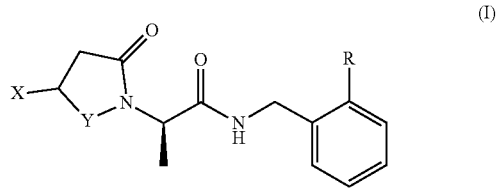

(I)

51 Claims, 9 Drawing Sheets

(56) References Cited

OTHER PUBLICATIONS

Ferreri et al., (2004) "Comparative Anticonvulsant Activity of N-Acetyl-1-Aryl-6, 7-Dimethoxy-1, 2, 3, 4-Tetrahydroisoquinoline Derivatives in Rodents", Pharmacology Biochemistry and Behavior, 77(1):85-94.
Kaminski et al., (2020) "N-Benzyl-(2, 5-dioxopyrrolidin-1-yl) propanamide (AS-1) with Hybrid Structure as a Candidate for a Broad-Spectrum Antiepileptic Drug", Neurotherapeutics, 17(1):309-328.
Lemieszek et al., ( Oct. 1, 2018) "Neuroprotective properties of Cantharellus cibarius polysaccharide fractions in different in vitro models of neurodegeneration", Carbohydrate Polymers, 197:598-607.
Lubelska et al., (2019) "Are the Hydantoin-1,3,5-triazine 5-HT6R Ligands a Hope to a Find New Procognitive and Anti-Obesity Drug? Considerations Based on Primary In Vivo Assays and ADME-Tox Profile In Vitro", Molecules, 24 (24):4472 (24 pages).
Mogilski et al., (2017) "Aryl-1,3,5-triazine ligands of histamine H4 receptor attenuate inflammatory and nociceptive response to carrageen, zymosan and lipopolysaccharide", Inflammation Research, 66:79-95.
Pytka et al., (2017) "HBK-15 protects mice from stress-induced behavioral disturbances and changes in corticosterone, BDNF, and NGF levels", Behavioural Brain Research, 333:54-66.
Pytka et al., (2018) "HBK-17, a 5-HT1A Receptor Ligand With Anxiolytic-Like Activity, Preferentially Activates ß-Arrestin Signaling", Frontiers in Pharmacology, 9:Article 1146, 13 pages.
Riban et al., (2002) "Evolution of Hippocampal Epileptic Activity during the Development of Hippocampal Sclerosis in a Mouse Model of Temporal Lobe Epilepsy", Neuroscience, 112(1):101-111.
Salat et al., (2014) "Antiallodynic and Antihyperalgesic Activity of 3-[4-(3-trifluoromethyl-phenyl)-piperazin-1-yl]-dihydrofuran-2-one Compared to Pregabalin in Chemotherapy-Induced Neuropathic Pain in Mice", Pharmacology Biochemistry and Behavior, 122:173-181.
Salat et al., (2017) "Antinociceptive, antiallodynic and antihyperalgesic effects of the 5-HT1A receptor selective agonist, NLX-112 in mouse models of pain", Neuropharmacology, 125:181-188 (26 pages).
Salpekar et al., (Sep. 2019) "Common psychiatric comorbidities in epilepsy: How big of a problem is it?", Epilepsy & Behavior, 98(Pt B):293-297 (5 pages).
Schmued et al., (Aug. 25, 2000) "Fluoro-Jade B: a high affinity fluorescent marker for the localization of neuronal degeneration", Brain Research, 874(2):123-130.
Socala et al., (2018) "KA-11, A Novel Pyrrolidine-2,5-Dione Derived Broad-Spectrum Anticonvulsant: its Antiepileptogenic, Antinociceptive Properties and in Vitro Characterization", ACS Chemical Neuroscience, 10(1):636-648 (41 pages).
Tanabe et al., (2008) "Zonisamide suppresses pain symptoms of formalin-induced inflammatory and streptozotocin-induced diabetic neuropathy", Journal of pharmacological sciences, 107(2):213-220.
Tang et al., (Jul. 6, 2017) "Drug-Resistant Epilepsy: Multiple Hypotheses, Few Answers", Frontiers in Neurology, 8: Article 301, (19 pages).
Thapar et al., (Jan. 2009) "Stress, anxiety, depression, and epilepsy: Investigating the relationship between psychological factors and seizures", Epilepsy & Behavior, 14(1):134-140.
Wojda et al., (2009) "Isobolographic Characterization of Interactions of Levetiracetam with the Various Antiepileptic Drugs in the Mouse 6 Hz Psychomotor Seizure Model", Epilepsy Research, 86(2-3):163-174.

\* cited by examiner

MODIFIED AMINO ACID DERIVATIVES FOR THE TREATMENT OF NEUROLOGICAL DISEASES AND SELECTED PSYCHIATRIC DISORDERS

Cross-Reference To Related Applications

This application is a U.S. National Phase Application of PCT/PL2020/050028, filed on Apr. 16, 2020, which claims priority to Polish Patent Application Serial No. P.429656 filed on Apr. 16,2019, all of which are hereby incorporated by reference in their entirety.

FIELD OF THE INVENTION

The invention relates to chemical compounds that are structurally modified amino acid derivatives and their use as active substance in various dosage forms of the drug.

The disclosed compounds exhibit broad protective activity in animal models of epileptic seizures, pain models, depression and anxiety model, and, what is extremely important, are deprived of the sedative effect that is characteristic of well-known antiepileptic drugs. The results of in vivo studies indicate their potential use in the therapy of neurological disorders (epilepsy, neuropathic pain and migraine) and psychiatric disorders (including anxiety and depression). Given the wide range of therapeutic indications for antiepileptic drugs, these compounds may also be useful, among others, for the treatment of withdrawal syndrome, schizophrenia, schizoaffective disorder, personality and nutrition disorders, and post-traumatic stress. The disclosed compounds may also be effective in the treatment of neurodegenerative diseases (including Parkinson's disease, Alzheimer's disease, amyotrophic lateral sclerosis, etc.) and central nervous system damage caused by hypoxia.

STATE OF THE ART

Epilepsy is one of the most common and extremely debilitating neurological diseases. This disease affects 1-2% of the human population and significantly reduces the quality of life of patients at all levels—personal, professional and social. One of the main factors determining the deterioration in the quality of life of epileptic patients is depression, which occurs in up to 55% of epileptic patients, while in the general population this percentage is about 15% (Salpekar et al. *Epilepsy Behav.* 2019, 98, 293-297). It has also been proven that depression can be a significant risk factor for epilepsy. There are also more frequent cases of anxiety disorder and psychosis among patients with epilepsy (Thapar et al. *Epilepsy Behav.* 2009, 14, 134-140). Currently, medicine has a number of antiepileptic drugs that have been divided into three generations, taking into account the time of their introduction onto the pharmaceutical market. It should be emphasized that the latest preparations belonging to the third generation of drugs (e.g. lacosamide, rufinamide, eslicarbazepine, brivaracetam, perampanel), despite much rarer and less severe side effects, do not outweigh the effectiveness of less tolerated first generation drugs (e.g. phenytoin, valproic acid, carbamazepine). In addition, the latest preparations have mostly a narrow range of therapeutic indications and are dedicated only to a given type of epilepsy. It has also been proven that drugs affecting central GABAergic conductance (including vigabatrin, topiramate, and tiagabine) cause a deterioration in the mood of patients using them. In addition, all antiepileptic drugs currently in treatment have a lower or greater undesirable sedative effect (in monotherapy this effect is least pronounced for gabapentin (approx. 9% of patients) and lamotrigine (approx. 10% of patients), while the strongest for phenobarbital (approx. 39% of patients), phenytoin (approx. 32% of patients) and levetiracetam (approx. 20% of patients). Both depressed mood and sedative effects are common causes of discontinuation of planned treatment. It should be added that due to the complex pathophysiology, epilepsy is an extremely heterogeneous disease, i.e. it is characterized by the occurrence of various types of seizures (e.g. including tonic-clonic epilepsy, absence epilepsy, focal onset seizures, etc.) and significant drug resistance, reaching ~30-40% of diagnosed cases (Tang et al. *Front. Neurol.* 2017, 8, 301).

Considering the above facts, a breakthrough in pharmacotherapy of epilepsy will be obtaining a drug effective in various types of epileptic seizures, effective in the drug-resistant epilepsy, deprived of sedative effects, and also reducing the severity of epileptic coexisting disorders, i.e. anxiety and, above all, depression. Currently, there is no such preparation in medicine.

The object of the present invention is to provide compounds with the desired characteristics confirmed in preclinical studies.

SUMMARY OF THE INVENTION

The subject of the invention is a compound of formula (I):

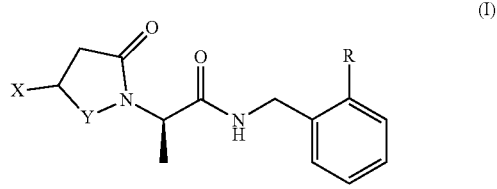

where:
X is hydrogen or $N(CH_3)_2$,
Y is $CH_2$ or $C=O$,
R is hydrogen or halogen, preferably F,
or pharmaceutically acceptable salts thereof.
Preferably, the compound according to the invention is selected from:
(2R)—N-benzyl-2-(2,5-dioxopyrrolidin-1-yl)propanamide,
(2R)-2-(2,5-dioxopyrrolidin-1-yl)—N-(2-fluorobenzyl)propanamide,
(2R)—N-benzyl-2-(2-oxopyrrolidin-1-yl)propanamide,
(2R)—N-(2-fluorobenzyl)-2-(2-oxopyrrolidin-1-yl)propanamide,
(2R)—N-benzyl-2-(3-(dimethylamino)-2,5-dioxopyrrolidin-1-yl)propanamide and
(2R)-2-(3-(dimethylamino)-2,5-dioxo-pyrrolidin-1-yl)—N-(2-fluorobenzyl)propanamide.

Particularly preferably, the compound according to the invention is selected from: (2R)—N-benzyl-2-(2,5-dioxopyrrolidin-1-yl)propanamide and (2R)-2-(2,5-dioxopyrrolidin-1-yl)—N-(2-fluorobenzyl)propanamide.

Particularly preferably, the compound according to the invention is selected from: (2R)—N-benzyl-2-(2-oxopyrrolidin-1-yl)propanamide, (2R)—N-(2-fluorobenzyl)-2-(2-oxopyrrolidin-1-yl)propanamide, (2R)—N-benzyl-2-(3-(dimethylamino)-2,5-dioxopyrrolidin-1-yl)propanamide and (2R)-2-(3-(dimethylamino)-2,5-dioxopyrrolidin-1-yl)—N-(2-fluorobenzyl)propanamide, especially (2R)—N-benzyl- 2-(3-(dimethylamino)-2,5-dioxopyrrolidin-1-yl)propanamide and (2R)-2-(3-(dimethylamino)-2,5-dioxopyrrolidin-1-yl)—N-(2-fluorobenzyl)propanamide.

Preferably, the compound according to the invention is in the form of a pharmaceutically acceptable salt selected from: hydrochloride, sulfate, methanesulfonate, toluenesulfonate, succinate, fumarate or lactate.

A further object of the invention is a compound according to the invention, as defined above, for use in the treatment or prevention of epilepsy, epilepsy associated with depressive and anxiety disorders, depression, anxiety, neurological pain, inflammatory pain or neurodegenerative disease.

Preferably, the neurodegenerative disease is Parkinson's disease or Alzheimer's disease or amyotrophic lateral sclerosis.

In a preferred embodiment, the invention relates to a 2-(2,5-dioxopyrrolidin-1-yl)propanamide or 2-(2-oxopyrrolidin-1-yl)propanamide derivative with R-configuration of the stereogenic center, selected from: (2R)—N-benzyl-2-(2,5-dioxopyrrolidin-1-yl)propanamide (1), (2R)-2-(2,5-dioxopyrrolidin-1-yl)—N-(2-fluorobenzyl)propanamide (2), (2R)—N-benzyl-2-(2-oxopyrrolidin-1-yl)propanamide (3), (2R)—N-(2-fluorobenzyl)-2-(2-oxopyrrolidin-1-yl)propanamide (4), (2R)—N-benzyl-2-(3-(dimethylamino)-2,5-dioxopyrrolidin-1-yl)propanamide (5) and (2R)-2-(3-(dimethylamino)-2,5-dioxopyrrolidin-1-yl)—N-(2-fluorobenzyl)propanamide (6), the general structure of which is represented by formula (I):

Where:

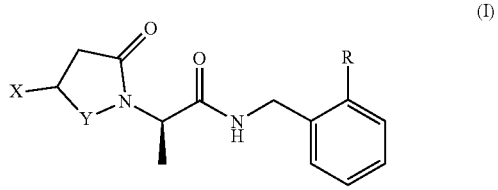

Compound 2: X=H, Y=C=O, R=F
Compound 3: X=H, Y=CH$_2$, R=H
Compound 4: X=H, Y=CH$_2$, R=F
Compound 5: X=N(CH$_3$)$_2$, Y=C=O, R=H
Compound 6: X=N(CH$_3$)$_2$, Y=C=O, R=F Due to the presence of the tertiary amine group in the structure of compounds 5 and 6, these derivatives form water-soluble salts. Pharmaceutically acceptable salts include, but are not limited to, hydrochlorides, sulfates, methanesulfonates, toluenesulfonates, succinates, fumarates, lactates, etc. These salts, as well as other pharmaceutically acceptable compounds having a salt character, are the subject of this invention.

Another subject is a compound according to the invention as defined above for use in the treatment or prevention of epilepsy, epilepsy associated with depressive and anxiety disorders, depression, anxiety, neurological pain, inflammatory pain or neurodegenerative disease. Preferably, the neurodegenerative disease is Parkinson's disease or Alzheimer's disease or amyotrophic lateral sclerosis.

DETAILED DESCRIPTION OF THE INVENTION 2-(2,5-Dioxopyrrolidin-1-yl)propanamide or 2-(2-oxopyrrolidin-1-yl)propanamide derivatives are disclosed, preferably compounds represented by formulas 1-6 with the R-configuration of the stereogenic center.

These compounds revealed high protective efficacy in the in vivo preclinical studies applying various animal models of human epileptic seizures, i.e. the maximal electroshock seizure test (MES), subcutaneous pentylenetetrazole seizure test (scPTZ) and the 6 Hz (32 mA and/or 44 mA) seizure model after intraperitoneal administration to mice. Substances with such a pharmacological profile are potentially effective in a wide spectrum of human epileptic seizures, namely tonic-clonic seizures with or without secondary generalization, myoclonic seizures, generalized absence seizures, focal onset seizures, and drug-resistant seizures. The compounds according to the invention are completely devoid of any negative effect on the motor coordination of mice in the rotarod test, which is a measure of the neurotoxicity of the acute substance. This is an important feature that distinguishes them from currently used anticonvulants, which, with a few exceptions (levetiracetam), lead to impairment of the motor coordination of animals at doses similar to or higher than those effective. Thus, the compounds according to the invention possess much broader spectrum of activity and are characterized by an incomparably higher safety profile (in the rotarod test) compared to all currently used antiepileptic drugs. Another unique feature of the compounds according to the invention is that they are completely devoid of the sedative effect that is characteristic of known antiepileptic drugs (including levetiracetam). This effect was evaluated in the spontaneous locomotor activity test in mice. The results of the aforementioned test further proved that the compounds according to the invention unexpectedly increase slightly the spontaneous locomotor activity of the animals at doses at which their anticonvulsant effect was observed. This effect is dose-dependent and it is a completely unique and unseen feature among all antiepileptic drugs used in therapy. An increase in spontaneous mouse locomotor activity may be attributed to, among others, antidepressant activity of a substance, and this effect has been confirmed in the forced swim test (Porsolt test). In addition, anxiolytic activity was also demonstrated in the four plates test (Aron test). These are further important pharmacological properties that distinguish the compounds according to the invention from the currently used and tested antiepileptic drugs. Locomotor activity stimulation also indicates a potentially new mechanism of action for the substances included in the present invention (which, however, has not yet been defined). Another added value of the above compounds is an antinociceptive effect in the formalin test, in the oxaliplatin- and the streptozotocin-induced pain model in mice, which clearly indicates the potential utility of the above substances for the treatment of pain of various origins, including chemotherapy-induced neuropathy and diabetic neuropathy.

The compounds according to the present invention are structurally enantiomers with R absolute configuration of the previously disclosed racemic mixtures of (2RS)—N-benzyl-2-(2,5-dioxopyrrolidin-1-yl)propanamide and (2RS)-2-(2,5-dioxopyrrolidin-1-yl)—N-(2-fluorobenzyl)propanamide (Kamiński, et al. Bioorg. Med. Chem. 2015, 23, 2548-2561; Rapacz, et al. Naunyn Schmiedeberg's Arch. Pharmacol. 2017, 6, 567-579). Surprisingly, the enantiomers having R absolute configuration not described so far showed a significantly higher anticonvulsant activity compared to the above-mentioned racemates (RS) and enantiomers with the S configuration. In addition, the compounds according to the invention increase the spontaneous locomotor activity of mice, which was not observed in the case of the S enantiomer and previously disclosed racemates (Rapacz, et al. *Naunyn Schmiedeberg's Arch. Pharmacol.* 2017, 6, 567-579). It should also be emphasized that racemic mixture consists of two compounds with different configurations within the asymmetric center. Individual enantiomers may have different pharmacodynamic, pharmacokinetic and toxicological properties, therefore, the racemic mixture does not meet the criteria for drug candidates. Considering the more favorable pharmacological properties of R enantiomers, the present invention relates to isolated compounds with R configuration of the stereogenic center.

Compounds of formulas (1-6) have a chiral center at the acetamide linker, the scope of the invention includes enantiomers with the R configuration of the stereogenic center of said fragment. These compounds can be obtained using the appropriate isomeric forms of the starting material (amino acid derivatives) or can be separated after preparation of the final compound in the form of a racemic mixture according to known separation methods. The advantage of compounds 3-6 compared to 1 and 2 is their good water solubility, which should result in better pharmaceutical availability of the substance, which translates into more favorable pharmacokinetics, including first of all better absorption from the gastrointestinal tract and higher bioavailability after their oral administration. In addition, good water solubility allows parenteral administration of the preparation, which is primarily desirable for achieving a rapid therapeutic effect in emergency situations, i.a. to quickly stop an epileptic seizure.

The second aspect of the invention is the use of compounds described by formula (1-6) as active substance in pharmaceutical compositions for the treatment of epileptic seizures or neurological and inflammatory pain or migraine or depression or anxiety or neurodegenerative diseases (including Parkinson's, Alzheimer's disease, multiple sclerosis lateral atrophic, etc.) or damage to the central nervous system due to hypoxia. The compounds according to the invention possess anticonvulsant, analgesic, antidepressant and anxiolytic activity in a wide panel of animal models and can find use as active substances of various forms of the drug for the treatment of epilepsy, epilepsy associated with depressive and anxiety disorders, depression, anxiety, neurological pain, inflammatory pain, neurodegenerative diseases (including Parkinson's, Alzheimer's disease, amyotrophic lateral sclerosis, etc.), central nervous system damage caused by hypoxia.

Compounds of formula (1-6) according to the invention can be obtained according to multi-step procedure using commercially available and tert-butoxycarbonyl (Boc) protected D-alanine (with R absolute configuration) as starting material.

In the first step, the condensation reaction of the appropriate primary amine with a tert-butoxycarbonyl (Boc) protected D-alanine group yields the intermediate product of formula (II), which subsequently forms the desired primary amine of general formula (III) as a result of the deprotection reaction. Step i and ii are common to all compounds (1-6). In the case of derivatives 1 and 2, in the next step the amine of formula (III) is subjected to a condensation reaction with succinic anhydride to obtain the compound of the amino acid structure of formula (IV). The intermediate (IV) forms the desired compounds of formula (1 and 2) applying the cyclization reaction. The synthetic procedure and reaction conditions are illustrated in Scheme 1.

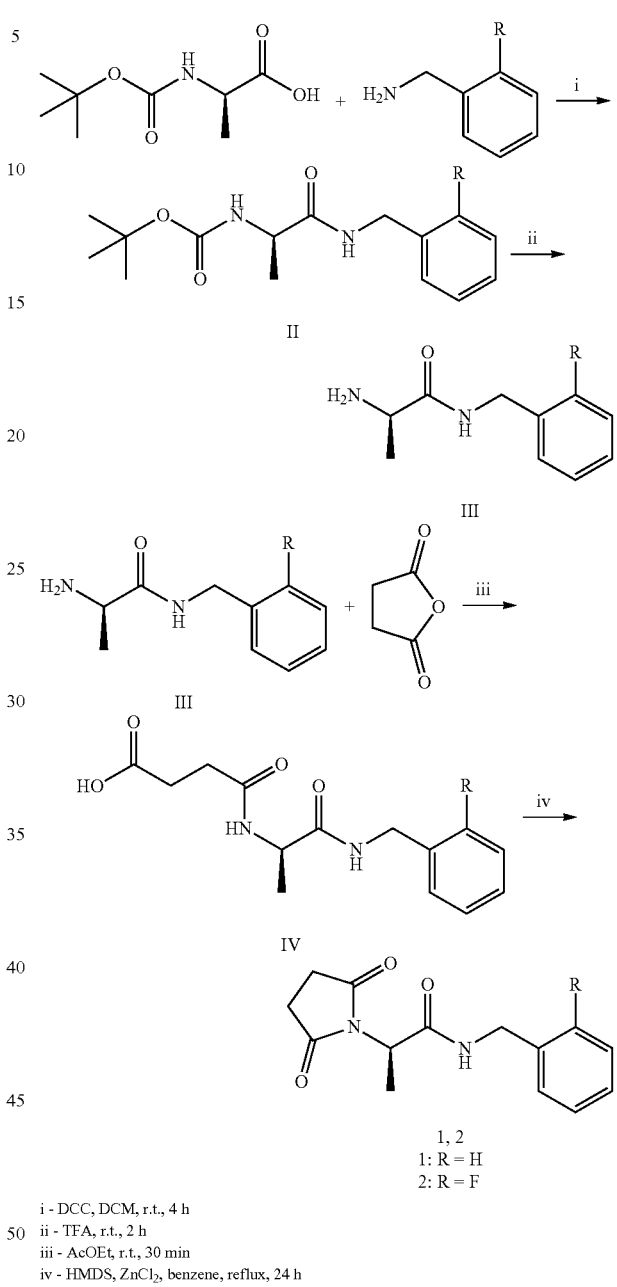

Scheme 1. The synthesis of compounds (1 and 2) according to the invention.

i - DCC, DCM, r.t., 4 h
ii - TFA, r.t., 2 h
iii - AcOEt, r.t., 30 min
iv - HMDS, ZnCl$_2$, benzene, reflux, 24 h In the case of pyrrolidin-2-one derivatives (3 and 4), the primary amine (III) is subjected to an acylation reaction with 4-chlorobutanoic acid chloride to obtain derivative (V). Compound V, as a result of a cyclization reaction in the presence of an alkaline agent, i.a. sodium hydride, forms the desired products 3 and 4. Alternatively to 4-chlorobutanoic acid, 4-bromo- or 4-iodobutanoic acid can be used in the acylation reaction. The synthetic procedure of compounds 3 and 4 is illustrated in Scheme 2.

Scheme 2. The synthesis of compounds (3 and 4) according to the invention.

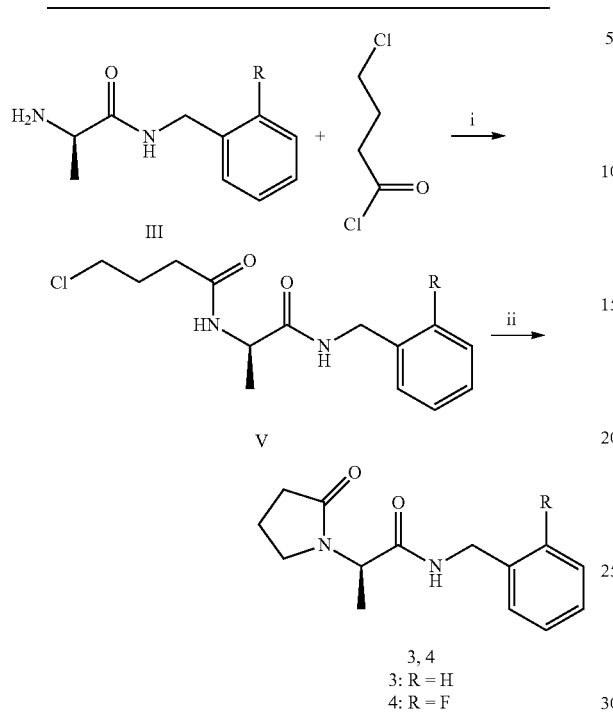

i - DCM, TEA, r.t., 30 min
ii - NaH, THF, r.t., 4 h

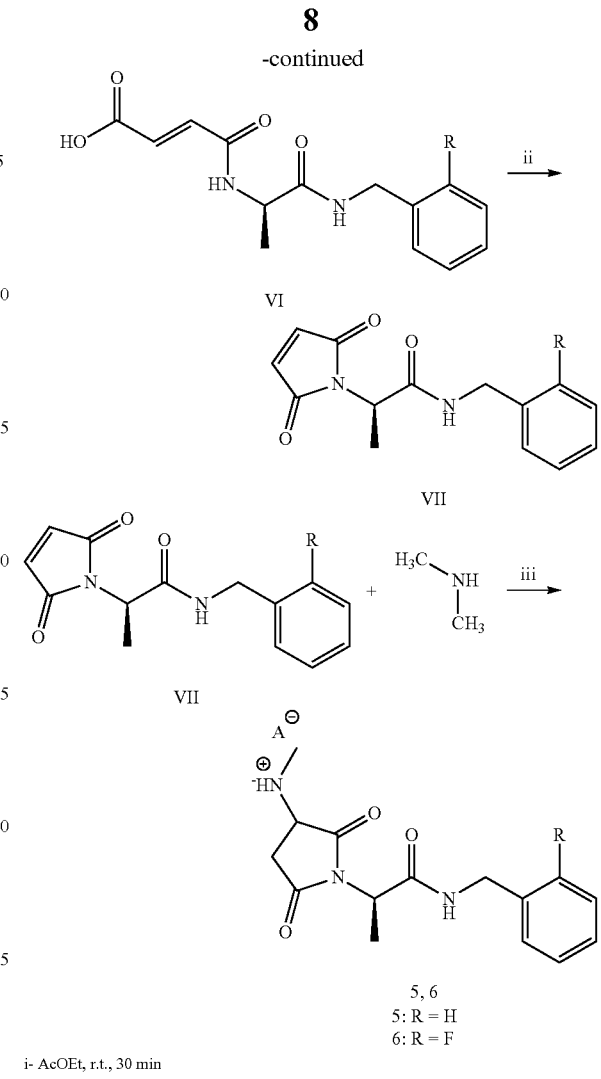

i- AcOEt, r.t., 30 min
ii - HMDS, ZnCl$_2$, benzene, r.t, 24 h
iii - 1) benzene, r.t., 2 h, 2) HA, solvent Similarly to compounds 1-4, salt derivatives (5, 6) are obtained using the primary amine (III) as a substrate. Compound III subjected to a condensation reaction with maleic anhydride forms a monounsaturated acid (VI). This compound forms a maleinimide derivative (VII) as a result of the cyclization reaction. Derivative VII subjected to a dimethylamine addition reaction to a double bond forms a compound with the tertiary amine moiety in the structure that allows convertion into a water-soluble salt using methods described in the literature. Pharmaceutically acceptable salts include, but are not limited to, hydrochlorides, sulfates, methanesulfonates, toluenesulfonates, succinates, fumarates, lactates, etc. As examples, compounds 5 and 6 were obtained as hydrochlorides. The synthesis of compounds 5 and 6 is illustrated in Scheme 3.

Scheme 3. The synthesis of compounds (5 and 6) according to the invention.

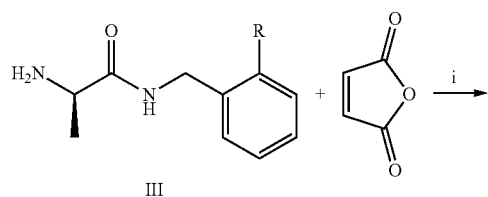

The solution according to the invention has several advantages. The disclosed compounds of formula (1 and 2) are characterized by strong and broad anticonvulsant activity in various animal models of epilepsy, i.e. the maximal electroshock seizure test (MES), subcutaneous pentylenetetrazole (scPTZ) seizure test and 6 Hz (32 mA and 44 mA) seizure model. Compounds with this profile in pre-clinical in vivo studies can be effective in various types of human epilepsy, including tonic-clonic seizures with or without secondary generalization, generalized seizures (absence), myoclonic seizures, focal onset seizures, and, importantly, drug-resistant seizures. Another advantage of the compounds of formula (1 and 2) is the stereospecificity of the pharmacological action, namely compounds with R absolute configuration have significantly stronger anticonvulsant activity in comparison with enantiomers with S configuration and appropriate racemic mixtures. A unique feature of the compounds included in the present invention is the fact that they are completely devoid of the sedative effect that was tested in the spontaneous locomotor activity test in mice. The results of this test further proved that the compounds according to the invention unexpectedly increase slightly the locomotor activity of the animals at the doses at which their anticonvulsant effect was observed. This suggests an antidepressant and anxiolytic effect, which has been proven for compound 1. Another advantage of the compounds of formula (1 and 2) is the antinociceptive activity in animal evaluation tests, i.e. in formalin test, in a oxaliplatin-induced neuropathic pain model and in the streptozotocin-induced model of diabetic neuropathy. Therefore, these compounds may find application in the therapy of neuropathic pain caused by chemotherapy, diabetes as well as inflammatory pain. Compounds according to formula (1 and 2) may also be potentially useful, among others, for the treatment of migraine, withdrawal syndrome, schizophrenia, schizoaffective disorders, personality and nutrition disorders, anxiety, post-traumatic stress, neurodegenerative diseases (e.g. Parkinson's disease, Alzheimer's disease, amyotrophic lateral sclerosis, etc.) and central nervous system damage caused by hypoxia. Compounds according to formula (1 and 2) have favorable ADME-Tox parameters in in vitro tests. Similar pharmacological properties should be observed for water-soluble compounds 3-6 according to the invention.

The compounds (1 and 2) according to the invention may be administered by a variety of routes, including enterally, topically or parenterally, using an appropriate pharmaceutical preparation suitable for given administration routes and containing at least one active compound according to formula (1 and 2) in pharmaceutically acceptable and effective amounts, together with pharmaceutically acceptable diluents, carriers and/or excipients known in the art. The preparation of such pharmaceutical formulations is known in the art. The therapeutic dose will vary depending on the substance, species, sex, age, disease entity being treated, route and method of administration, which must be determined by a person skilled in the art. The proposed dose of compounds of the invention is from 0.1 to about 1000 mg per day, in single or divided doses. The compounds according to the invention are administered to a patient as such or in combination with one or more other active ingredients, each in its own composition, or with some or all of the active ingredients combined in a single composition, and/or appropriate pharmaceutical excipients. Suitable pharmaceutical excipients include conventional excipients and formulation aids such as fillers, binders, disintegrants, lubricants, solvents, gel formers, emulsifiers, stabilizers, dyes and/or preservatives. The compounds of the invention are formulated into dosage forms using commonly known pharmaceutical methods of preparation. Dosage forms can be, e.g., tablets, capsules, granules, suppositories, emulsions, suspensions or solutions. Depending on the method of administration and the galenical form, the amount of active substance in the formulation may typically range from 0.01% and 100% (by weight).

In order to better explain the invention, the present description has been supplemented with the attached Figures.

FIG. 1 shows analgesic activity of compound 1 in the first and second phase of the formalin test. The results are presented as paw licking time in the first phase of the test (0-5 minutes after formalin injection) and in the second phase of the test (15-30 minutes after formalin injection). The values represent mean±SEM for a group of 8-10 animals. Statistically significant difference in comparison to the control group given only vehicle (Tween 80). One-way analysis of variance (ANOVA) followed by post-hoc Dunnett's test: *p<0.05, p<0.01, *p<0.001, ****p<0.0001. C—control group.

FIG. 2 shows the analgesic activity of compound 1 in the oxaliplatin-induced neuropathic pain model. The results show the pain threshold (stimulus at which the animal withdraws its paw) 30 minutes after administration of the compound. The values represent mean±SEM for a group of 10 animals. A statistically significant difference compared to the group given only oxaliplatin (one-way repeated-measures analysis of variance (ANOVA), Dunnett's post hoc test): *p<0.05, *p<0.001, **p<0.0001.

FIG. 3 shows the analgesic activity of compound 1 in the streptozotocin-induced model of painful diabetic neuropathy. The results show the pain threshold (stimulus at which the animal withdraws its paw) 30 minutes after administration of the compound. The values represent the mean±SEM for a group of 10 animals. A statistically significant difference compared to the group given the vehicle (1% Tween 80) (one-way repeated-measures analysis of variance (ANOVA), Dunnett's post hoc test): *p<0.05, *p<0.001, **p<0.0001.

FIG. 4 shows the antidepressant activity of compound 1 in the forced swim test. The results show the total immobility time during 4 minutes of observation of mice placed in a cylinder filled with water. The values represent mean±SEM for a group of 8-10 animals. A statistically significant difference compared to the control group given the vehicle alone (1% Tween 80) (one-way analysis of variance (ANOVA), Dunnett's post hoc test): ***p<0.001.

FIG. 5 shows the anxiolytic activity of compound 1 in the four plate test. The results show the total number of electrically punished plate crossings during 60 seconds of observation of mice placed in specialized cages. The values represent mean±SEM for a group of 8-10 animals A statistically significant difference compared to the control group given the vehicle alone (1% Tween 80) (one-way analysis of variance (ANOVA), Dunnett's post hoc test): ***p<0.001.

FIGS. 6A and 6B show the effect of compound 1 and 2 on the spontaneous locomotor activity of animals. The results show the number of infrared light beams interruptions during 30 minutes of measurement. The values represent mean ±SEM for a group of 10 animals. A statistically significant difference compared to the control group (one-way repeated-measures analysis of variance (ANOVA), Dunnett's post hoc test): *p<0.05, **p<0.01.

FIGS. 7A-7F show the neuroprotective properties of test compound 1 after PILO-induced SE (A—control mouse+PILO, B-F–compound 1+PILO).

FIG. 8A shows the effect of the reference inhibitor ketoconazole (KE) and 1 on CYP3A4 activity. FIG. 8B shows the effect of the reference inhibitor quinidine (QD) and 1 on CYP2D6 activity. FIG. 8C shows the effect of the reference inhibitor sulfafenazole (SE) and 1 on CYP2C9 activity. Statistical significance was calculated by one-way analysis of variance (ANOVA) and the Bonferroni method (*p<0.05, ***p<0.001, compounds tested in triplicate).

Figure 12A:
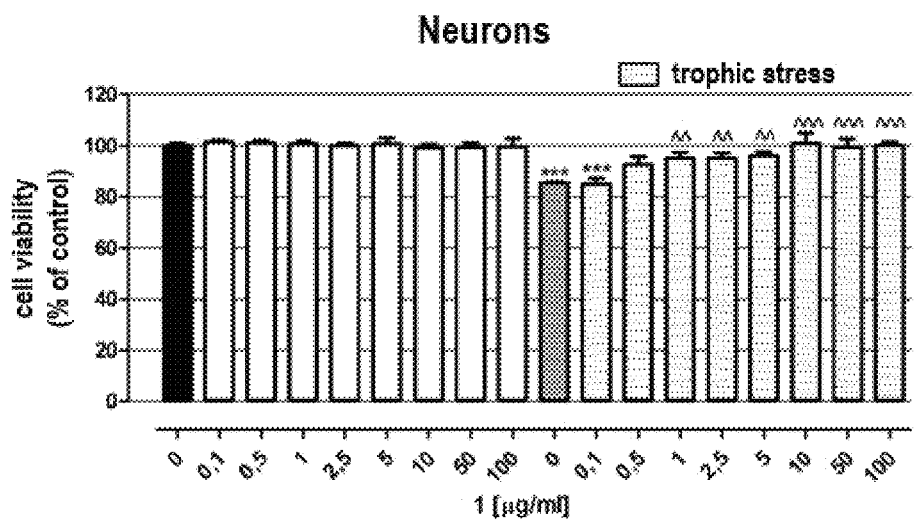
Figure 12B:
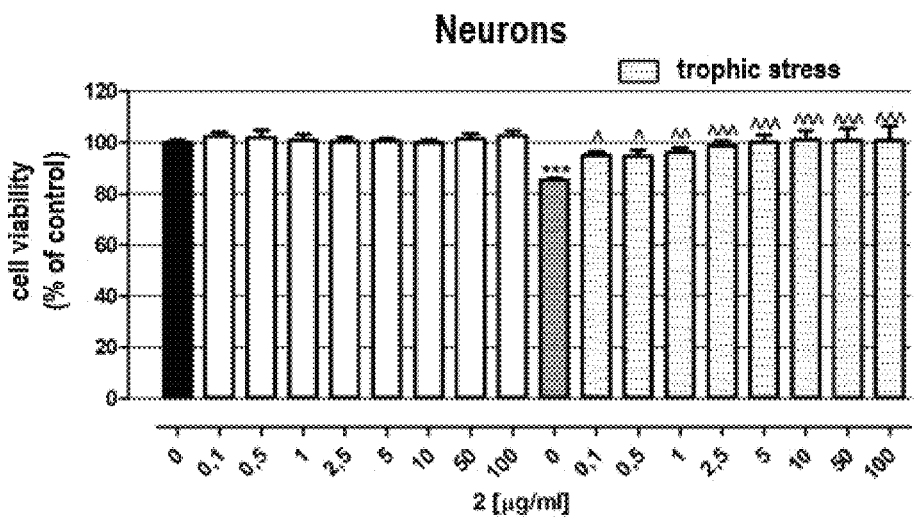

FIGS. 12A and 12B show the neuroprotective properties of compounds 1 and 2 against human neurons derived from SH-SY5Y neuroblastoma cells under trophic stress. Viability of neurons was determined by MTT test after 48 hours exposure to test compounds under standard conditions and trophic stress induced by removal of the B27 supplement from the culture medium. The results are presented as the mean±SD of at least 6 measurements. Statistically significant differences compared to controls at ***$p<0.001$; compared to cells grown in medium without B27 *$p<0.05$, $p<0.01$, *$p<0.001$. Statistical analysis was performed by one-way ANOVA with Tukey's post-hoc test.

The following are examples of embodiments of the invention.

EXAMPLE 1. PREPARATION OF COMPOUNDS ACCORDING TO THE INVENTION

Analytical Methods:

Proton magnetic resonance ($_1$H NMR) and carbon nuclear magnetic resonance ($_{13}$C NMR) spectra were recorded using a JEOL-500 spectrometer (JEOL USA, Inc. MA, USA), at 500 MHz and 126 MHz, respectively. Chemical shifts are reported in δ values (ppm) relative to TMS δ=0 ($_1$H) as an internal standard. The J values are expressed in hertz (Hz). Deuterated chloroform (CDCl$_3$) was used as the solvent. The following signal abbreviations have been used in the description of the spectra: s (singlet), br s (broad singlet), d (doublet), t (triplet), q (quartet), m (multiplet). The UPLC/MS analysis system consisted of a Waters ACQUITY® UPLC® apparatus (Waters Corporation, Milford, Mass., USA) coupled with a Waters TQD mass spectrometer operating in electrospray ionization (ESI) mode. Chromatographic separations were carried out using an Acquity UPLC BEH C18 (2.1×100 mm, 1.7 μm) column. The column was maintained at 40° C. and eluted with a gradient of 95% to 0% of eluent A over 10 min, with a flow rate of 0.3 mL/min. Eluent A: water/formic acid (0.1%, v/v); eluent B: acetonitrile/formic acid (0.1%, v/v). Chromatograms were recorded using a Waters eλ PDA detector. Spectra were analyzed in the 200-700 nm range with a resolution of 1.2 nm and a sampling rate of 20 points/s. Enantiomeric purity of compounds 1-4 was determined using a chiral HPLC chromatograms analysis on a Shimadzu Prominence and LC-2030C SD Plus apparatus (Shimadzu Corporation, Kyoto, Japan) equipped with an Amylose-C (250×4.6 mm) chiral column. The analysis was performed under the following conditions: column temperature: 20° C., eluent mixture: hexane/i-PrOH=85/15 (v/v), flow rate: 0.7 mL/min, detection at λ=209 nm. For intermediate VII, the analysis was performed under the following conditions: column temperature: 33° C., eluent mixture: hexane/i-PrOH/TFA=93.4/6.4/0.2 (v/v/v), flow rate: 0.75 mL/min, detection at λ=206 nm. Specific rotation ($[\alpha]_{20D}$) of compounds was tested on a Jasco p-2000 polarimeter (Jasco Inc. Easton, MD, USA). Thin layer chromatography (TLC) was performed on aluminum plates precoated with silica gel 60 F$_{254}$ (Macherey-Nagel, Duren, Germany), using solvent systems with the following composition: DCM:MeOH (9:0.3; v/v), DCM:MeOH (9:0.5; v/v). Spot detection—UV light (λ=254 nm). Melting points (m.p.) were determined using open capillaries in a Büchi 353 apparatus (Büchi Labortechnik, Flawil, Switzerland). Absolute configuration was confirmed by crystallographic method using a SuperNova diffractometer (Rigaku—Oxford Diffraction, UK). The names of the chemical compounds described below as exemplary embodiments of the invention were obtained using the ChemBioDraw Ultra 12.0 program.

The preparation of compounds according to the invention is illustrated in the following examples. The synthesis presented in the examples were not optimized in terms of yield, amount of reagents used or the final form of the compounds obtained.

Abbreviations used: AcOEt—ethyl acetate, DCM—dichloromethane, DCC—N,N'-dicyclohexylcarbodiimide, Et$_2$O—diethyl ether, HCl—hydrochloric acid, HMDS—hexamethyldisilazane, MeOH—methanol, NaCl—sodium chloride, NaH—sodium hydride, NH$_4$OH—ammonium hydroxide, Na$_2$SO$_4$—sodium sulfate, TFA—trifluoroacetic acid, TEA—triethylamine, ZnCl$_2$—zinc chloride.

Examples of Synthesis as Well as Physicochemical and Spectral Data of Intermediate Products (II-IV) According to Scheme 1

Intermediate II (R=H): Tert-butyl-(R)-(1-(benzylamino)-1-oxopropan-2-yl)carbamate Boc-D-alanine (5.1 g, 27 mmol, 1 eq) was dissolved in 20 mL of DCM, then DCC (6.68 g, 32.4 mmol, 1.2 eq) was added, the mixture was stirred and after 30 minutes benzylamine (2.89 g, 27 mmol, 1 eq) was added dropwise. The reaction evaporated to dryness. Intermediate II was purified by column chromatography using a DCM:MeOH (9:0.3; v/v) eluent system. Intermediate II was obtained as a light oil. Yield: 91% (6.95 g); TLC:R$_f$=0.43 (DCM:MeOH (9:0.3; v/v)); C$_{15}$H$_{22}$N$_2$O$_3$ (278.35), monoisotopic mass: 278.16. UPLC (100% purity): t$_R$=5.44 min. (M+H)+279.3.

Intermediate III (R=H): (R)-2-amino-N-benzylpropanamide 10 ml of TFA was added to a solution of tert-butyl-(R)-(1-(benzylamino)-1-oxopropan-2-yl)carbamate (6.95 g, 25 mmol, 1 eq) (II) in DCM (40 mL) and the whole reaction mixture was stirred for 2 hours. TFA was then neutralized with a 25% NH$_4$OH solution, followed by extraction with DCM (3×50 mL). The organic layer was dried over anhydrous Na$_2$SO$_4$, then DCM was evaporated to dryness. (R)-2-Amino-N-benzylpropanamide (III) was obtained as a light oil. Yield: 89% (3.9 g); TLC:R$_f$=0.21 (DCM:MeOH (9:0.5; v/v)); C$_{10}$H$_{14}$N$_2$O (178.24), monoisotopic mass: 178.11. UPLC (96.8% purity): t$_R$=2.11 min. (M+H)+179.2.

Intermediate IV (R=H): (R)-4-((1-(benzylamino)-1-oxopropan-2-yl)amino)-4-oxobutanoic acid Succinic anhydride (2.19 g, 21 mmol, 1 eq) was added to a solution of (R)-2-amino-N-benzylpropanamide (3.9 g, 21 mmol, 1 eq) (III) in AcOEt (40 mL) and the whole mixture was stirred for 30 minutes. After this time, AcOEt was distilled off to dryness. The compound was obtained in solid form after washing with Et$_2$O. White solid. Yield: 95% (5.80 g); m.p. 129.8-131.4° C.; TLC:R$_f$=0.34 (DCM:MeOH (9:0.5; v/v)); C$_{14}$H$_{18}$N$_2$O$_4$ (278.31), monoisotopic mass: 278.13. UPLC (98.4% purity): t$_R$=3.23 min. (M+H)+279.2.

Synthesis and Physicochemical and Spectral Data of Final Compounds 1 and 2

Compound 1: (2R)—N-benzyl-2-(2,5-dioxopyrrolidin-1-yl)propanamide

ZnCl$_2$ (1.36 g, 10 mmol, 1 eq) was added to the suspension of (R)-4-((1-(benzylamino)-1-oxopropan-2-yl)amino)-

4-oxobutanoic acid (2.78 g, 10 mmol, 1 eq) (IV, R═H) in dry benzene (40 mL) and the whole mixture was heated to 80° C. with stirring. Then a solution of HMDS (2.42 g, 3.14 ml, 15 mmol, 1.5 eq) in dry benzene (15 mL) was added dropwise over 30 minutes. The reaction was continued with stirring at reflux for about 24 hours and then concentrated under reduced pressure. After distilling off the solvent, the oily residue was dissolved in DCM (50 mL) and extracted with 0.1 M HCl (3×50 mL), water (3×50 mL) and saturated NaCl solution (3×50 mL). The organic layer was dried over anhydrous $Na_2SO_4$ and then evaporated to dryness. The crude product was purified by column chromatography using DCM:MeOH (9:0.3; v/v) eluent system. The compound was obtained as a solid after washing with $Et_2O$. White solid. Yield: 90% (2.34 g); m.p. 138.2-138.9° C.; Chiral HPLC>99% ee ($t_R$=22.649 min); $[\alpha]_{20D}$+51.52° (c 0.1%, DCM); TLC:$R_f$=0.39 (DCM:MeOH (9:0.3; v/v)); $C_{14}H_{16}N_2O_3$ (260.29), monoisotopic mass: 260.12. UPLC (100% purity): $t_R$=3.94 min. (M+H)+261.1. $^1$H NMR (500 MHz, $CDCl_3$) δ 1.56 (d, J=7.5 Hz, 3H), 2.66 (s, 4H), 4.39 (d, J=5.7 Hz, 2H), 4.76 (q, J=7.3 Hz, 1H), 6.45 (br s, 1H), 7.22-7.26 (m, 3H), 7.30-7.32 (m, 2H). $_{13}$C NMR (126 MHz, $CDCl_3$) δ 14.5, 24.9, 25.6, 28.3, 33.7, 43.8, 49.8, 127.6, 127.7, 128.8, 137.9, 168.6, 177.0.

Compound 2: (2R)-2-(2,5-dioxopyrrolidin-1-yl)—N-(2-fluorobenzyl)propanamide

The compound was prepared using the procedure analogous to that described for the synthesis of compound 1. (R)-4-((1-((2-fluorobenzyl)amino)-1-oxopropan-2-yl)amino)-4-oxobutanoic acid (2.96 g, 10 mmol, 1 eq) (IV, R═F), $ZnCl_2$ (1.36 g, 10 mmol, 1 eq) and HMDS (2.42 g, 3.14 ml, 15 mmol, 1, 5 eq) were used in the reaction. The crude product was purified by column chromatography using DCM:MeOH (9:0.3; v/v) eluent system. White solid. Yield: 89% (2.48 g); m.p. 115.1-115.8° C.; Chiral HPLC>99% ee ($t_R$=24.859 min); $[\alpha]_{20D}$+27.90° (c 0.1%, DCM); TLC:$R_f$=0.43 (DCM:MeOH (9:0.3; v/v)); $C_{14}H_{15}FN_2O_3$ (278.28), monoisotopic mass: 278.11. UPLC (100% purity): $t_R$=4.08 min, (M+H)+279.2. $^1$H NMR (500 MHz, $CDCl_3$) δ 1.56 (d, J=7.5 Hz, 3H), 2.68 (s, 4H), 4.43 (t, J=6.0 Hz, 2H), 4.73-4.76 (m, 1H), 6.50 (br s, 1H), 7.00 (t, J=9.1 Hz, 1H), 7.08 (t, J=7.5 Hz, 1H), 7.21-7.28 (m, 1H), 7.29-7.31 (m, 1H). 13C NMR (126 MHz, $CDCl_3$) δ 14.5, 28.2, 37.9, 37.9, 49.8, 115.3, 115.5, 124.5, 124.8, 124.9, 129.4, 129.4, 130.2, 130.2, 160.0, 161.9, 168.8, 176.9.

Example of Synthesis as Well as Physicochemical and Spectral Data of Intermediate (V) According to Scheme 2

Intermediate V (R═H) (R)—N-(1-(benzylamino)-1-oxopropan-2-yl)-4-chlorobutanamide 4-Chlorobutanoic acid chloride (0.59 g, 4.2 mmol, 1.5 eq) and TEA (0.85 g, 8.4 mmol, 3 eq) were added to a solution of (R)-2-amino-N-benzylpropanamide (0.50 g, 2.8 mmol, 1 eq) (III) in DCM (20 mL) and the whole reaction mixture was stirred for 0.5 hour. Then DCM was evaporated to dryness. Intermediate V was purified by column chromatography using DCM:MeOH (9:0.5; v/v) eluent system. Intermediate V was obtained as a light oil. Yield: 82% (0.65 g); TLC:$R_f$=0.53 (DCM:MeOH (9:0.5; v/v)); $C_{14}H_{19}ClN_2O_2$ (282.77), monoisotopic mass: 282.11. UPLC (97.8% purity): $t_R$=4.52 min. (M+H)+283.2.

Synthesis and Physicochemical and Spectral Data of Final Compounds 3 and 4

Compound 3: (2R)—N-benzyl-2-(2-oxopyrrolidin-1-yl)propanamide

NaH (0.106 g, 4.4 mmol, 2 eq) was added to a solution of (R)—N-(1-(benzylamino)-1-oxopropan-2-yl)-4-chlorobutanamide (0.63 g, 2.2 mmol, 1 eq) (V, R═H) in anhydrous THF, the hole reaction mixture was stirred for 4 hours and then concentrated under reduced pressure. After distilling off the solvent, the oily residue was dissolved in 0.1 M HCl (50 mL) and extracted with DCM (3×50 mL). The organic layer was dried over anhydrous $Na_2SO_4$ and then evaporated to dryness. The crude product was purified by column chromatography using DCM:MeOH (9:0.5; v/v) eluent system. The compound was obtained as a solid after washing with $Et_2O$. White solid. Yield: 86% (0.47 g); m.p. 96.7-97.5° C.; Chiral HPLC>99% ee ($t_R$=10.623 min); TLC:$R_f$=0.42 (DCM:MeOH (9:0.5; v/v)); $C_{14}H_{15}N_2O_2$ (246.31), Monoisotopic Mass: 264.13. UPLC (purity: >99.9%): $t_R$=3.92 min, (M+H)+247.2. $^1$H NMR (500 MHz, $CDCl_3$) δ 1.36 (d, J=7.2 Hz, 3H), 1.95-1.99 (m, 2H), 2.28-2.36 (m, 2H), 3.36-3.43 (m, 2H), 4.38 (dd, J=5.9, 2.2 Hz, 2H), 4.65-4.74 (m, 1H), 6.75 (br s, 1H), 7.19-7.22 (m, 2H), 7.23-7.25 (m, 1H), 7.27-7.31 (m, 2H). $_{13}$C NMR (126 MHz, $CDCl_3$) δ 13.8, 18.1, 31.1, 43.5, 43.8, 50.3, 127.5, 127.6, 128.7, 138.3, 170.6, 175.8.

Compound 4: (2R)—N-(2-fluorobenzyl)-2-(2-oxopyrrolidin-1-yl)propanamide

The compound was prepared using the procedure analogous to that described for the synthesis of compound 3. (R)-4-chloro-N-(1-((2-fluorobenzyl)amino)-1-oxopropan-2-yl)butanamide (0.57 g, 1.9 mmol, 1 eq) (V, R═F) and NaH (0.091 g, 3.8 mmol, 2 eq) were used in the reaction. The crude product was purified by column chromatography using DCM:MeOH (9:0.5; v/v) eluent system. White solid. Yield: 88% (0.44 g); m.p. 92.5-93.1° C.; Chiral HPLC>99% ee ($t_R$=8.959 min); TLC:$R_f$=0.39 (DCM:MeOH (9:0.5; v/v)); $C_{14}H_{17}FN_2O_2$ (264.30), Monoisotopic Mass: 264.13. UPLC (purity: >99.9%): $t_R$=4.04 min, (M+H)+265.9. $^1$H NMR (500 MHz, $CDCl_3$) δ 1.34 (d, J=7.2 Hz, 3H), 1.96-2.00 (m, 1H), 2.27-2.44 (m, 2H), 3.30-3.34 (m, 1H), 3.39-3.42 (m, 1H), 4.39 (dd, J=14.9, 5.7 Hz, 1H), 4.47 (dd, J=15.0, 6.2 Hz, 1H), 4.64-4.75 (m, 1H), 4.69 (d, J=7.2 Hz, 1H), 6.69 (br s, 1H), 7.01 (t, J=9.1 Hz, 1H), 7.07 (t, J=7.4 Hz, 1H), 7.21-7.27 (m, 2H). $_{13}$C NMR (126 MHz, $CDCl_3$) δ 13.7, 18.1, 31.1, 37.6, 37.7, 43.7, 50.3, 115.4, 115.5, 124.3, 124.3, 125.1, 125.3, 129.3, 129.4, 130.0, 130.1, 160.0, 162.0, 170.6, 175.8.

Examples of Synthesis as Well as Physicochemical and Spectral Data of Intermediate Products (VI, VII) According to Scheme 3

Intermediate VI (R═H) (R)-4-((1-(benzylamino)-1-oxopropan-2-yl)amino)-4-oxobut-2-enoic acid Maleic anhydride (0.33 g, 3.4 mmol) was added to a solution of (R)-2-amino-N-benzylpropanamide (0.6 g, 3.4 mmol, 1 eq) (III) in AcOEt (40 mL, 1 eq) and the whole mixture was stirred for 30 minutes. After this time, AcOEt was evaporated to dryness. The compound was obtained in solid form after washing with Et$_2$O. White solid. Yield: 98% (0.91 g); TLC:R$_f$=0.28 (DCM:MeOH (9:0.1; v/v)); C$_{14}$H$_{16}$N$_2$O$_4$ (276.29), monoisotopic mass: 276.11. UPLC (purity >99.9%): t$_R$=3.72 min. (M+H)$_+$ 278.2.

Intermediate VII (R=H) (R)—N-benzyl-2-(2,5-dioxo-2,5-dihydro-1H-pyrrol-1-yl)propanamide ZnCl$_2$ (0.39 g, 10 mmol, 1 eq) was added to the suspension of (R)-4-((1-(benzylamino)-1-oxopropan-2-yl)amino)-4-oxobut-2-enoic acid (0.80 g, 2.9 mmol, 1 eq) (VI, R=H) in dry benzene (20 mL) and heated to 80° C. with stirring. Then a solution of HMDS (0.70 g, 0.91 mL, 4.35 mmol, 1.5 eq) in dry benzene (8 mL) was added dropwise over 30 minutes. The reaction was continued with stirring at reflux for about 24 hours and then concentrated under reduced pressure. After distilling off the solvent, the oily residue was dissolved in DCM (50 mL) and extracted with 0.1 M HCl (3×50 mL), water (3×50 mL) and saturated NaCl solution (3×50 mL). The organic layer was dried over anhydrous Na$_2$SO$_4$ and then evaporated to dryness. The crude product was purified by column chromatography using DCM:MeOH (9:0.5; v/v) eluent system. The compound was obtained as a solid after washing with Et$_2$O. White solid. Yield: 80% (0.60 g); m.p. 98.3-98.8° C.; Chiral HPLC>99% ee (t$_R$=50.631 min); TLC:R$_f$=0.34 (DCM:MeOH (9:0.5; v/v)); C$_{14}$H$_{14}$N$_2$O$_3$ (258.28), monoisotopic mass: 258.10. UPLC (100% purity): t$_R$=4.41 min. (M+H)$_+$ 259.2.

Synthesis and Physicochemical and Spectral Data of Final Compounds 5 and 6

Compound 5: (2R)—N-benzyl-2-(3-(dimethylamino)-2,5-dioxopyrrolidin-1-yl)propanamide hydrochloride 2M solution of dimethylamine (0.105 g, 2.3 mmol, 1 eq) in THF was added to a solution of (R)—N-benzyl-2-(2,5-dioxo-2,5-dihydro-1H-pyrrol-1-yl)propanamide (0.60 g, 2.3 mmol, 1 eq) (VII, R=H) in dry benzene (30 mL). The crude product was purified by column chromatography using DCM:MeOH (9:0.5; v/v) eluent system. The compound was then converted into the hydrochloride salt by treating the compound with a 2M methanolic hydrochloric acid solution. White solid. Yield: 88% (0.62 g); m.p. 115.8-116.9° C.; TLC:R$_f$=0.36 (DCM:MeOH (9:0.5; v/v)); C$_{16}$H$_{22}$ClN$_3$O$_3$ (339.82), Monoisotope mass (calculated for: C$_{16}$H$_{21}$N$_3$O$_3$): 303.16. UPLC (purity: >99.9%): t$_R$=2.79 min, (M+H)$_+$ 304.2. $^1$H NMR (500 MHz, CDCl$_3$) δ 1.52 (d, J=7.2 Hz, 3H), 2.78 (s, 6H), 2.85 (br s, 3H), 4.34 (d, J=6.0 Hz, 2H), 4.74-4.77 (m, 1H), 7.18-7.24 (m, 2H), 7.25-7.29 (m, 3H), 7.59 (br s, 1H), 7.73 (br s, 1H). $_{13}$C NMR (126 MHz, CDCl$_3$) δ 14.2, 14.2, 31.0, 32.1, 32.2, 41.8, 42.1, 43.6, 49.9, 50.0, 61.0, 61.3, 127.3, 127.4, 127.6, 127.8, 128.6, 128.6, 138.5, 138.6, 167.9, 168.1, 171.8.

Compound 6: (2R)-2-(3-(dimethylamino)-2,5-dioxopyrrolidin-1-yl)—N-(2-fluorobenzyl) propanamide hydrochloride The compound was prepared using the procedure analogous to that described for the synthesis of compound 5. 2-(2,5-Dioxo-2,5-dihydro-1H-pyrrol-1-yl)—N-(2-fluorobenzyl)propanamide (0.64 g, 2.3 mmol, 1 eq) (VII, R=F) and a 2M solution of dimethylamine (0.105 g, 2.3 mmol, 1 eq) in THF were used in the reaction. The crude product was purified by column chromatography using DCM:MeOH (9:0.5; v/v) eluent system. The compound was then converted into the hydrochloride salt by treating the compound with a 2M methanolic hydrochloric acid solution. White solid. Yield: 85% (0.63 g); m.p. 118.4-119.6° C.; TLC: R$_f$=0.45 (DCM:MeOH (9:0.5; v/v)); C$_{16}$H$_{21}$ClFN$_3$O$_3$ (357.81), Monoisotope mass (calculated as: C$_{16}$H$_{20}$FN$_3$O$_3$): 321.15. UPLC (purity: >99.9%): t$_R$=2.91 min, (M+H)$_+$ 322.2. $^1$H NMR (500 MHz, CDCl$_3$) δ 1.52 (dd, J=11.5, 7.5 Hz, 3H), 2.94 (s, 6H), 3.08-3.36 (m, 3H), 4.38-4.44 (m, 2H), 4.76 (dd, J=15.0, 7.30 Hz, 1H), 6.93-7.01 (m, 1H), 7.03-7.10 (m, 1H), 7.19 (dd, J=4.7, 2.2 Hz, 1H), 7.26-7.33 (m, 1H), 7.61 (br s, 1H), 7.8 (br s, Hz, 1H). $_{13}$C NMR (126 MHz, CDCl$_3$) δ 14.2, 31.0, 32.2, 32.4, 37.5, 50.0, 50.0, 60.9, 61.2, 115.2, 115.3, 115.3, 124.3, 129.1, 129.2, 129.8, 130.0, 159.8, 161.7, 167.9, 168.0, 171.4.

EXAMPLE 2. BIOLOGICAL ACTIVITY OF COMPOUNDS ACCORDING TO THE INVENTION

In Vivo Studies

The study was conducted on male Swiss albino mice (CD-1) weighing 18-26 g. All procedures were carried out in accordance with applicable Polish and international guidelines on the ethics of animal testing, after obtaining appropriate institutional approval. The substances 1-2 were administered intraperitoneally (i.p.), after suspension in a 1% aqueous Tween 80 solution, as single injections with a volume of 10 ml/kg of body weight, 30 minutes before the given test. Anticonvulsant activity and the effect on motor coordination in the rotarod test after intragastric (p.o.) administration to mice were also evaluated for compound 1. In these studies, compound 1 was administered in a volume of 10 ml/kg by oral gavage after its dissolution in a mixture of DMSO, PEG 400, water for injection (10/40/50, v/v/v), 60 minutes before the given test. Compound 1 was also tested for anticonvulsant activity as part of the American search program for new antiepileptic drugs—ETSP (Epilepsy Therapy Screening Project), which is implemented by the National Institute of Neurological Disorders and Stroke, National Institutes of Health (NIH, Bethesda, Md., USA). These studies were carried out on individuals of male C57 black mice (Charles River) and individuals of male Sprague-Dawley rats. All tests were carried out based on the procedures described in the specialist literature.

Determination of In Vivo Anticonvulsant Activity

Screening was performed on groups of 4-8 mice or 4-8 rats. The median effective dose (ED$_{50}$) in a given test was estimated based on the results obtained in 3-4 groups of animals consisting of at least 6 individuals. All tests were carried out based on the procedures described in the specialist literature: maximal electroshock seizure test (Kamiński et al. *Bioorg. Med. Chem.* 2015, 23, 2548-2561; Castel-Branco et al. *Methods Find. Exp. Clin. Pharmacol.* 2009, 31, 101-106, Riban et al. *Neurosci.* 2002, 112, 101-111); 6 Hz (32 mA and/or 44 mA) seizure model (Barton et al. *Epilepsy Res.* 2001, 47, 217-227; Wojda et al. *Epilepsy Res.* 2009, 86, 163-174); subcutaneous pentylenetetrazole (scPTZ) seizure test (Ferreri et al. *Pharmacol. Biochem. Behav.* 2004, 77, 85-94), corneal kindled seizure model, lamotrigine resistant amygdala kindled seizure model.

Determination of In Vivo Antinociceptive Activity in Mice

All tests/models were carried out based on the procedures described in the specialist literature: formalin test (Beirith et al. *Eur. J. Pharmacol.* 1998, 345, 233-245), a model of oxaliplatin-induced neuropathic pain—von Frey test (Salat et al. *Pharmacol. Biochem. Behav.* 2014, 122, 173-181), streptozotocin-induced model of painful diabetic neuropathy (Salat et al. *Neuropharmacology* 2017, 125, 181-188; Tanabe et al. *J. Pharmacol. Sci.* 2008, 107, 213-220). The study group consisted of 8-10 animals.

Forced Swim Test (Porsolt Test) in Mice

To assess the potential antidepressant effect, a forced swim test was carried out in accordance with the methodology described in the scientific literature (Pytka et al. *Behav Brain Res.* 2017, 333, 54-66). The study group consisted of 8-10 animals.

Four Plates Test (Aron Test) in Mice

The potential anti-anxiety activity of the compounds tested was assessed using a four plates test according to the methodology described in the specialist literature (Pytka et al. *Front. Pharmacol.* 2018, 9, 627-13). The study group consisted of 8-10 animals.

Spontaneous Locomotor Activity Test in Mice

The assessment of the influence of the tested compounds on the spontaneous locomotor activity of animals (assessment of the sedative or activating effect) was carried out in accordance with the methodology described in the scientific literature (Mogilski et al. *Inflamm. Res.* 2017, 66, 79-95). The study group consisted of 10 animals.

Assessment of the Influence on the Motor Coordination of Mice in the Rotarod Test The effect of test compounds on the motor coordination in mice was assessed in a rotarod test (the apparatus—May Commat, RR 0711 Rota Rod, Turkey was used) according to the procedure described in the literature (Dunham et al. *J. Am. Pharm. Assoc.* 1957, 46, 64-66). These studies were also carried out in rats according to the methodology described by ETSP. The toxic dose ($TD_{50}$) in the rotarod test was estimated based on the results obtained in 3-4 groups of animals consisting of at least 6 individuals.

Neuroprotective Activity in the Pilocarpine-Induced Seizures

To assess the neuroprotective properties of compound 1, studies using pilocarpine (PILO) as a neurodegenerative agent were carried out. The dose of compound 1 determined in the 6 Hz (32 mA) test was used for the study. At the peak of compound 1 activity, the animals received PILO at a dose of 300 mg/kg (intraperitoneally) to induce status epilepticus (SE). 30 min before PILO administration, the mice received methylscopolamine (1 mg/kg) to reduce the PILO peripheral cholinergic effect. 72 hours later, animals were transcardially perfused (0.9% saline, followed by freshly prepared 4% paraformaldehyde) for brain collection for further analysis using the Fluoro-Jade B (FJB) immunofluorescence method (Schmued et al. Brain Res. 2000, 874, 123-130). Qualitative analysis was performed using a Nikon AIR confocal microscope (Tokyo, Japan).

Statistical Analysis

The $ED_{50}$ (effective dose) and $TD_{50}$ (toxic dose) values along with the corresponding 95% confidence limits were calculated based on the Litchfield and Wilcoxon method. To perform a statistical evaluation of the results, one-way analysis of variance (ANOVA) followed by Dunnett's post hoc test (multiple comparison test) were used. The values were considered statistically significant if $p<0.05$.

In Vitro Studies

Effects on Cytochrome P-450 Isoforms CYP3A4, CYP2D6 and CYP2C9

The studies were conducted using commercial luminescence tests CYP3A4 P450-Glo™, CYP2D6 P450-Glo™ and CYP2C9 P450-Glo™ from Promega (Madison, Wis., USA). Detailed methodology is described in the literature (Socala et al. *ACS Chem. Neurosci.* 2019, 10, 636-648, Kamiński et al. *Neurotherapeutics* 2020, 17, 309-328).

Plasma Protein Binding

Determination of binding parameters to two major plasma proteins—α1-glycoprotein (AGP) and human albumin (HSA) was performed using the TRANSIL-XL PPB Assay kit (Sovicell, Leipzig, Germany). Detailed methodology is described in the literature (Lubelska et al. *Molecules* 2019, 24, pii: E4472).

Metabolic Stability

The metabolic stability study was performed using human liver microsomes purchased from Sigma-Aldrich (St. Louis, Mo., USA). Detailed methodology is described in the literature (Kamiński et al. *Neurotherapeutics* 2020, 17, 309-328).

Assessment of Cytotoxic Activity Against the HaCaT Cell Line

Cell culture. The research material was the human HaCaT cell line (immortalized keratinocyte line) from the American Type Culture Collection (ATCC, Rockville, USA). Cells were cultured in DMEM medium (Dulbecco's Modified Eagle's Medium, Biowest SAS, France) with the addition of 10% fetal bovine serum, penicillin (100 U/ml), streptomycin (100 ug/ml) and HEPES (20 mM) at 37° C. with 5% $CO_2$ until 80% confluency is reached. Cells were then harvested using 0.25% trypsin-0.02% EDTA (Gibco Life Technologies, USA) and plated into 96-well plates ($1\times10_4$ per well) to check the cytotoxicity of test compounds by MTT assay.

MTT assay. The MTT assay (3-(4,5-dimethylthiazol-2-yl)-2,5-diphenyltetrazolium bromide) is based on the metabolic reduction of the tetrazole salt (MTT) to formazan, which occurs under the influence of mitochondrial succinate dehydrogenase active in living cells. Test cells were preincubated for 24 hours at 37° C. with 5% $CO_2$, then the medium was removed and the medium with the addition of test compounds in the concentration range from 140 to 20 μM was added. HaCaT cells cultured in the appropriate medium without the test compound were a control. After 72 h incubation, the medium was removed and MTT solution (0.5 mg/mL) dissolved in serum-free medium was added in a volume of 200 μL/well. After a 4-hour incubation at 37° C., the cells were washed with a 1:1 mixture of DMSO (dimethyl sulfoxide) and isopropanol to release and dissolve the formazan crystals. The optical density of dissolved formazan crystals was measured with a UVM 340 reader (ASYS Hitech GmbH, Austria) at 570 nm. The $IC_{50}$ value was estimated using CompuSyn version 1.0.

Assessment of Cytotoxic Activity Against the HEK-293 Cell Line

Human embryonic kidney cell line HEK-293 and ATCC CRL-1573 were also used for safety tests. The HEK-293 line was cultured in DMEM medium (Dulbecco's Modified Eagle's Medium) with the addition of 10% bovine serum (FBS) from Gibco (Carlsbad, CA, USA) at 37° C. and an atmosphere containing 5% $CO_2$. Prior to testing, cells were plated onto Thermo Scientific Nunc™ 96-well transparent culture plates (Waltham, MA, USA) at a concentration of $1.5\times10_4$ cells per well and incubated for 24 hours. Then a 10 mM stock solution of the test compound was diluted in culture medium and added to the cells at final concentrations in the range of 0.1-100 μM (DMSO concentration in all wells was 1%). The reference compound—doxorubicin (DX) was applied at a concentration of 1 μM. After 72 hours of incubation at 37° C. and an atmosphere containing 5% $CO_2$, the medium with the compound was removed, and then fresh medium with diluted MTS reagent (CellTiter 96® AQueous Non-Radioactive Cell Proliferation Assay) supplied by Promega (Madison, WI, USA) was added. Plates were again incubated for 2 hours, followed by absorbance measurement at 490 nm with an Perkin Elmer EnSpire reader (Waltham, MA USA). Statistical significance was calculated by one-way analysis of variance (ANOVA) and the Bonferroni method. The compounds were tested in four replications.

Assessment of Hepatotoxicity Against the HepG2 Cell Line

HepG2 cell line, ATCC HB-8065 was used for potential hepatotoxicity studies. Detailed methodology is described in the literature (Socala et al. *ACS Chem. Neurosci.* 2019, 10, 636-648, Kamiński et al. *Neurotherapeutics* 2020, 17, 309-328).

Assessment of Neurotrophic Activity Against Human Neurons

The study was carried out with culture of neurons derived from human neuroblastoma SH-SY5Y cells (from the European Collection of Cell Cultures, Salisbury, UK). The neuroprotective properties of compounds 1 and 2 under trophic stress conditions, induced by removal of the B27 supplement from the culture medium, were determined by MTT assay after 48 hours exposure of neurons to test compounds at concentrations from 0.1 to 100 μg/mL. Statistical significance was tested using the one-way ANOVA with Tukey's post-hoc test. A detailed protocol of neuronal differentiation and assessment of the neuroprotective properties of a substance is described in the literature (Lemieszek et al. *Carbohydr. Polym.* 2018, 197, 598-607).

In Vivo Test Results

Anticonvulsant Activities

Compounds 1 and 2 according to the invention exhibit broad anticonvulsant activity by acting effectively in the MES, 6 Hz (32 mA/44 mA) and scPTZ tests after intraperitoneal administration to mice. The obtained results revealed that the substances with R-absolute configuration (compounds (R)-1 and (R)-2, Table 1), being embodiments of the invention, showed stronger anticonvulsant activity in the epileptic seizure models used in comparison to the S-enantiomers (compounds (S)-1 and (S)-2, Table 1) and the corresponding racemic mixtures (compounds (RS)-1 and (RS)-2, Table 1)). Data for R and S enantiomers and racemic mixtures are presented in Table 1.

TABLE 1

$ED_{50}$ (MES, scPTZ, 6 Hz test) and $TD_{50}$ (rotarod test) parameters values for compounds 1 and 2 (R configuration), S enantiomers and racemic mixtures (RS), and the reference antiepileptic drug (valproic acid) after intraperitoneal administration to Swiss albino mice (CD-1).

| Compound | $ED_{50}$ [mg/kg] | | | | $TD_{50}$ [mg/kg] Rotarod test | PI $TD_{50}/ED_{50}$ |
|---|---|---|---|---|---|---|
| | MES | 6 Hz (32 mA) | 6 Hz (44 mA) | scPTZ | | |
| (R)-1 | 66.3 (53.6-82.0) | 15.6 (9.1-26.9) | 41.6 (32.8-52.7) | 36.3 (15.5-73.5) | >500 | >7.5 (MES) >32.0 (6 Hz, 32 mA) >12.0 (6 Hz, 44 mA) >13.8 (scPTZ) |
| (S)-1 | 87.5 (69.5-110.2) | 28.8 (16.9-48.9) | 115.1 (107.9-122.7) | 52.7 (37.7-85.0) | >500 | >5.7 (MES) >17.4 (6 Hz, 32 mA) >4.3 (6 Hz, 44 mA >9.5 (scPTZ) |
| (RS)-1* | 67.6 (56.3-81.2) | 24.6 (18.1-33.5) | 75.41 (63.60-89.42) | 42.8 (24.4-74.9) | 347.6 (307.5-392.8) | 5.1 (MES) 14.1 (6 Hz, 32 mA) 8.1 (scPTZ) |
| (R)-2 | 33.0 (22.5-48.2) | 14.1 (8.4-23.5) | 37.2 (23.0-60.4) | 33.2 (29.3-37.5) | 298.8 (265.3-315.5) | 9.0 (MES) 21.2 (6 Hz, 32 mA) 8.0 (6 Hz, 44 mA |
| (S)-2 | 49.9 (44.7-55.8) | 62.9 (45.7-86.6) | ND | 78.8 (53.2-95.3) | 310.2 (275.5-342.8) | 9.0 (scPTZ) 6.2 (MES) 4.9 (6 Hz, 32 mA) 3.9 (scPTZ) |
| (RS)-2* | 54.9 (48.3-62.3) | 33.8 (11.0-103.7) | ND | 50.3 (34.7-72.6) | 300.9 (256.7-352.6) | 5.5 (MES) 8.9 (6 Hz, 32 mA) 6.0 (scPTZ) |
| VPA | 252.7 (220.1-290.2) | 130.6 (117.6-145.2) | 183.1 (143.5-233.7) | 239.4 (209.2-274.1) | 430.7 (407.9-454.9) | 1.7 (MES) 3.3 (6 Hz, 32 mA) 2.4 (6 Hz, 44 mA 1.8 (scPTZ) |

The compounds were tested 30 min after intraperitoneal administration;
MES - maximal electroshock seizure test;
6 Hz (32 mA) and 6 Hz (44 mA) - test of psychomotor seizures induced by low frequency 6 Hz electrical stimulus oapplying current intensity of 32 mA or 44 mA;
scPTZ - subcutaneous pentylenetetrazole seizure test;
Rota rod test - rotating rod test;
PI - protective index ($TD_{50}/ED_{50}$).
ND - no data available.
*The results for (RS)-1 and (RS)-2 were disclosed in publications: Kamiński, et al. *Bioorg. Med. Chem.* 2015, 23, 2548-2561; Rapacz, et al. *Naunyn Schmiedeberg's Arch. Pharmacol.* 2017,6, 567-579.
VPA - valproic acid.

The obtained results confirmed that compounds 1 and 2 (with R configuration) have a stronger anticonvulsant effect and more favorable protective indexes (PI) compared to S-enantiomers and racemic mixtures (RS). Surprisingly, in the case of compound 2 in the MES test, the racemic mixture (RS)-2 is characterized by the weakest activity. Importantly, compounds 1 and 2 exhibited significantly higher activity and a better safety profile (PI values) than valproic acid, which is a model antiepileptic drug with a wide range of therapeutic indications (generalized seizures: myoclonic seizures, tonic-clonic seizures, atonic seizures, absence seizure); focal onset seizures: simple or complex seizures, secondary generalized seizures, Lennox-Gastaut syndrome; treatment of manic episodes in bipolar disorder; migraine).

Further studies carried out for compound 1 revealed its strong anticonvulsant activity in the MES, 6 Hz (32 mA/44 mA) and scPTZ tests after their intragastric (per os) administration to mice. The substance given in this way is also characterized by weak acute neurotoxicity in the rotating bar test (rotarod), which translates into very favorable safety margins expressed by the protective index (PI) (Table 2).

TABLE 2

$ED_{50}$ (MES, scPTZ, 6 Hz test), $TD_{50}$ (rotarod test) and PI parameters values for compound 1 after intragastric (per os) administration to Swiss albino mice (CD-1).

| Compound | $ED_{50}$ [mg/kg] | | | | $TD_{50}$ [mg/kg] Rotarod test | PI $TD_{50}/ED_{50}$ |
|---|---|---|---|---|---|---|
| | MES | 6 Hz (32 mA) | 6 Hz (44 mA) | scPTZ | | |
| (R)-1 | 48.6 (42.4-55.8) | 40.3 (33.9-47.8) | 73.2 (57.4-93.4) | 83.5 (65.9-105.7) | 473.7 (454.7-493.4) | 9.7 (MES) 11.7 (6 Hz, 32 mA) 6.5 (6 Hz, 44 mA) 5.7 (scPTZ) |

The compound was tested 60 min after intragastric (per os) administration;
MES - maximal electroshock seizure test;
6 Hz (32 mA) and 6 Hz (44 mA) - test of psychomotor seizures induced by low frequency 6 Hz electrical stimulus oapplying current intensity of 32 mA or 44 mA;
scPTZ - subcutaneous pentylenetetrazole seizure test;
Rotarod test - rotating rod test;
PI - protective index ($TD_{50}/ED_{50}$).

Data obtained in mice after intragastric (per os) administration indicate good absorption of compound 1 from the gastrointestinal tract, passage through the liver and the possibility of achieving effective concentration in the central nervous system.

Compound 1, which is an embodiment of the present invention, is additionally characterized by strong protective activity in black C57 mice (Charles River) in the 6 Hz (44 mA) test, and the corneal kindled seizure model (Table 3). This substance was also effective in the MES test and lamotrigine resistant amygdala kindled seizure model in rats after intraperitoneal administration (Table 4).

TABLE 3

$ED_{50}$ (th e6 Hz, 44 mA test and the corneal kindled seizure model), $TD_{50}$ (rotarod test) and PIs for compound 1 after intraperitoneal administration to black C57 mice (Charles River).

| Compound | $ED_{50}$ [mg/kg] | | $TD_{50}$ [mg/kg] Rotarod test | PI $TD_{50}/ED_{50}$ |
|---|---|---|---|---|
| | 6 Hz (44 mA) | Corneal kindled seizure model | | |
| (R)-1 | 69.9 (45.2-93.6) | 38.1 (34.2-42.8) | >150 | >2.1 (6 Hz, 44 mA) >3.9 (Corneal kindled seizure model) |

The compound was tested 60 min after intraperitoneal administration;
6 Hz (44 mA)—test of psychomotor seizures induced by low frequency 6 Hz electrical stimulus oapplying current intensity of 44 mA;
Rotarod test—rotating rod test;
PI—protective index (TD50/ED50).

TABLE 4

Protective effect of compound 1 in the MES test and lamotrigine resistant amygdala kindled seizure model in rats after intraperitoneal administration

| Compound | $ED_{50}$ [mg/kg] MES | $TD_{50}$ [mg/kg] Rotarod test | PI $TD_{50}/ED_{50}$ |
|---|---|---|---|
| (R)-1 | 34.9 (27.1-44.7) | 253.8 (220.7-294.5) | 7.3 (MES) |
| | Lamotrigine resistant amygdala kindled seizure model | | |
| (R)-1 | Dosage: 70 mg/kg | Number of protected rats: 3 (protection—60%) | Number of rats tested: 5 |

The compound was tested 30 min after intraperitoneal administration.
PI—protective index (TD50/ED50).

The data presented in Tables 3 and 4 show the potential efficacy of compound 1 according to the invention in human generalized tonic-clonic seizures (MES test), focal onset seizures (corneal kindled seizure model) and drug-resistant seizures (6 Hz, 44 mA model and lamotrigine resistant amygdala kindled seizure model).

Summing up, the data obtained in the tests/models used in the preclinical assessment of anticonvulsant activity indicate that the compounds according to the invention, and in particular compound 1, is a promising candidate for antiepileptic drug with potential for efficacy in many types of human epilepsy, including drug-resistant epilepsy. The good tolerance of compound 1 expressed in the weak influence on the motor coordination of animals in the rotarod test and the very high divergence of the active dose to the toxic dose suggests the usefulness of the compounds according to the invention, in particular compound 1, in special populations including pediatric patients (children and adolescents) and elderly patients.

Antinociceptive Activity

Figure 1:
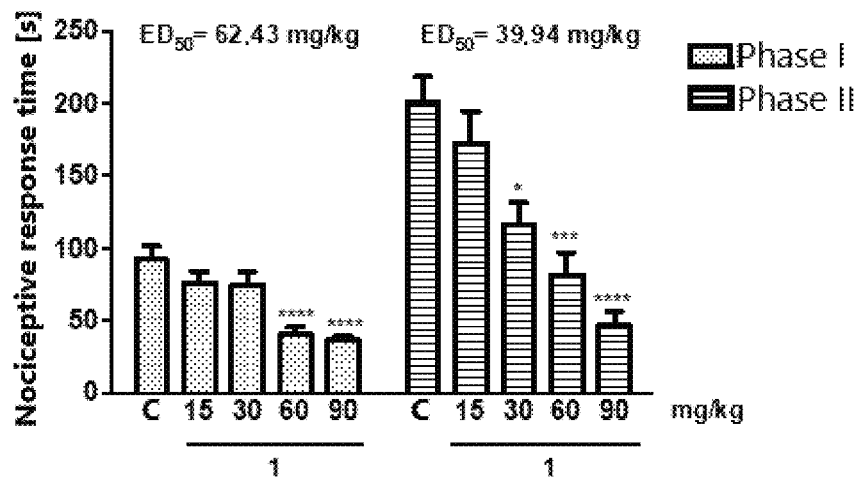

Formalin test: Compound 1 according to the invention showed distinct analgesic activity in both phases of the test. The mean nociceptive response time in the control group was 92.25±9.46 seconds and 200.60±18.28 seconds in the first and second phase of the test, respectively. Compound 1 reduced the nociceptive response time in the first phase of the formalin test, corresponding to acute pain, at all doses, with a statistically significant effect observed at the two highest doses—60 and 90 mg/kg. In the second phase of the test, corresponding to tonic inflammatory pain, compound 1 statistically significantly shortened the time of nociceptive response at doses of 30, 60 and 90 mg/kg (FIG. 1).

Figure 2:
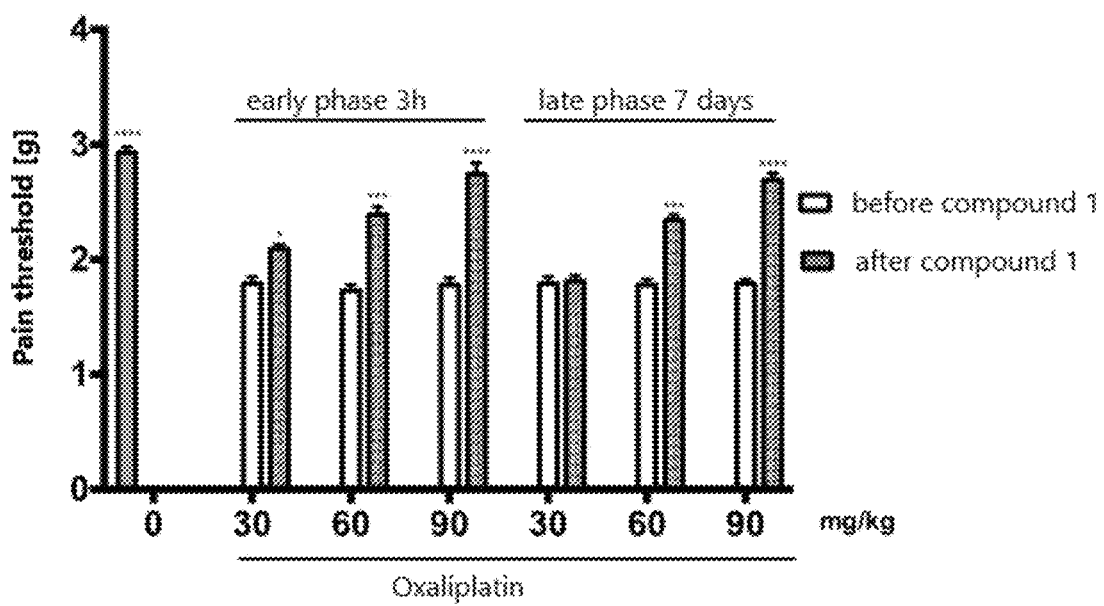

Oxaliplatin-induced neuropathic pain model—von Frey test: A single administration of oxaliplatin resulted in a lowering of the pain threshold in animals in response to a mechanical stimulus. The reaction was observed both 3 hours after administration of oxaliplatin (early phase) and 7 days after its administration (late phase). Test compound 1 administered at doses of 60 mg/kg and 90 mg/kg led to an increase in pain threshold at a dose-dependent manner, compared to the measurement made before the compound was administered. This compound at a dose of 30 mg/kg increased the pain threshold only in the early phase. The obtained results indicate that compound 1 has analgesic activity (reduces mechanical allodynia) in the oxaliplatin-induced neuropathic pain model (FIG. 2).

Streptozotocin-Induced Model of Diabetic Neuropathy—Von Frey Test

Figure 3:
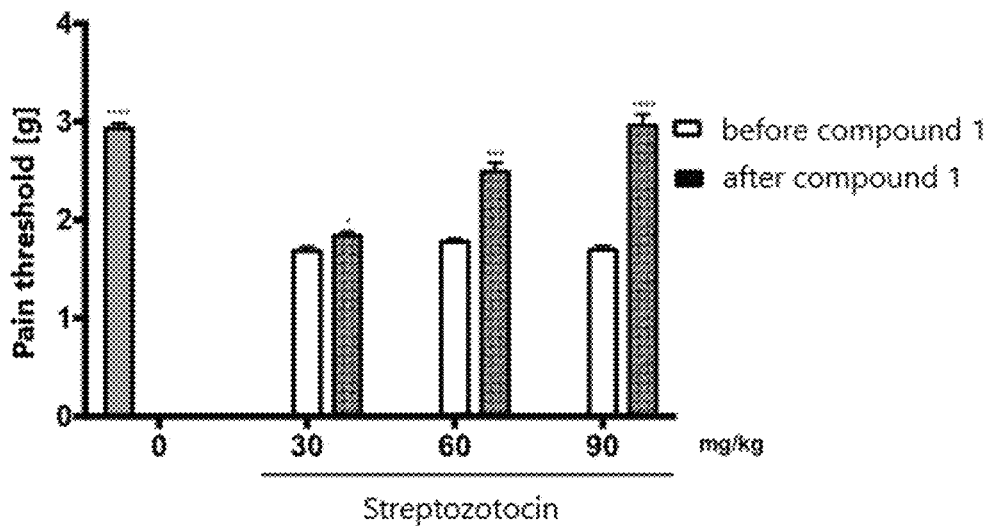

A single administration of streptozotocin resulted in the development of hyperglycemia (plasma glucose concentration exceeded 300 mg/dl) and a decrease in the pain threshold in animals in response to a mechanical stimulus (mechanical allodynia). The reaction was tested 3 weeks after streptozotocin injection. Test compound 1 administered at doses of 30 mg/kg, 60 mg/kg and 90 mg/kg led to an increase in the pain threshold in a statistically significant and dose-dependent manner, compared to the measurement made before the compound was administered. The compound at a dose of 90 mg/kg increased the pain threshold to the values observed before the induction of streptozotocin diabetes, and thus completely abolished the symptoms of developing sensory neuropathy. The obtained results indicate that compound 1 has analgesic activity (reduces mechanical allodynia) in the streptozotocin-induced model of diabetic neuropathy (FIG. 3).

Forced Swim Test (Porsolt Test)—Assessment of Antidepressant Effect

Figure 4:
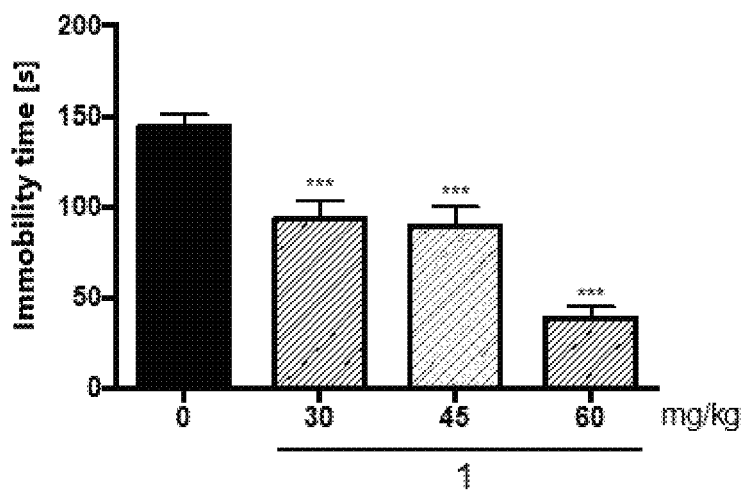

Test compound 1 administered at doses of 30 mg/kg, 45 mg/kg and 60 mg/kg statistically significantly shortened the immobility time in the forced swim test. The obtained results clearly indicate the potential antidepressant activity of the tested compound (FIG. 4).

Four Plates Test (Aron Test)—Evaluation of Anxiolytic Effect

Figure 5:
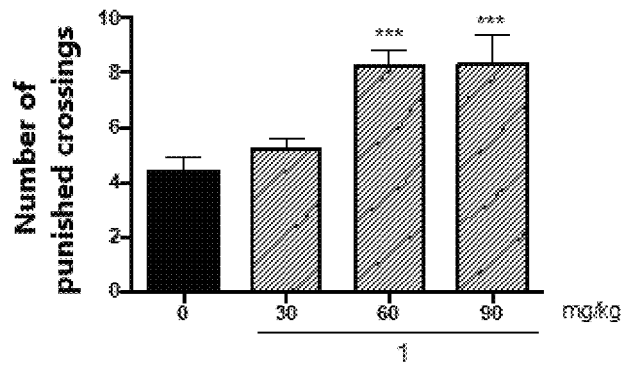

Test compound 1 administered at doses of 60 mg/kg and 90 mg/kg statistically significantly increased the number of electrically punished plate crossings. Administration of the test compound at a dose of 30 mg/kg did not result in a statistically significant difference compared to the control group given a vehicle. The results obtained indicate the anxiolytic effect of the compound. The effects of administration of 60 mg/kg and 90 mg/kg do not differ significantly, suggesting that the anxiolytic effect of the compound has a ceiling nature (FIG. 5).

Assessment of an Effect on Spontaneous Locomotor Activity of Mice

Figure 6A:
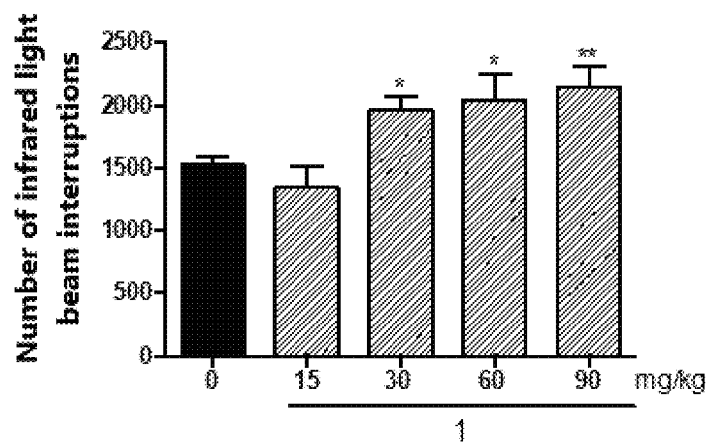
Figure 6B:
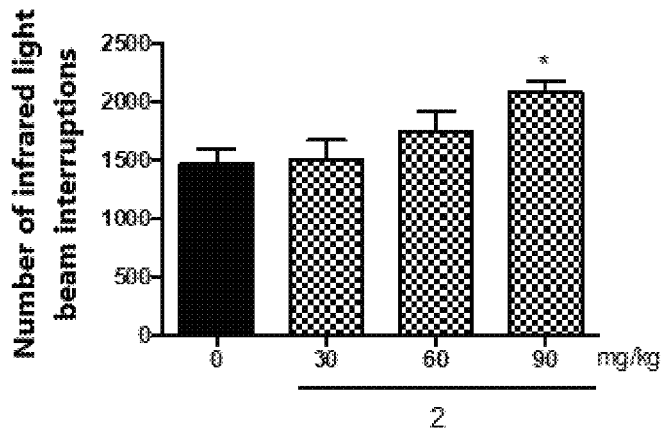

Compound 1 administered at 30 mg/kg, 60 mg/kg and 90 mg/kg doses statistically significantly increased the number of light beams interruptions in actometers during 30 minutes of measurement. The obtained result indicates that the tested compound increases the spontaneous locomotor activity of animals in the aforementioned dose range. For compound 2, a statistically significant increase in spontaneous locomotor activity of the mice was observed at a dose of 90 mg/kg (FIG. 6). These data confirm the lack of sedative effects of the disclosed compounds, which confirms their usefulness as drugs, including the special population, in children and adolescents.

Figure 7A:
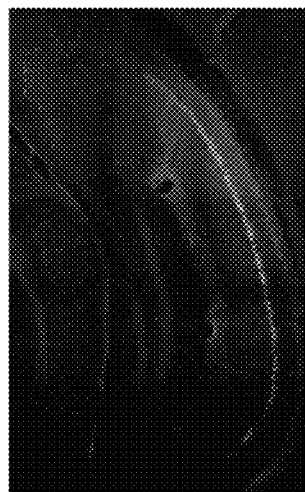
Figure 7B:
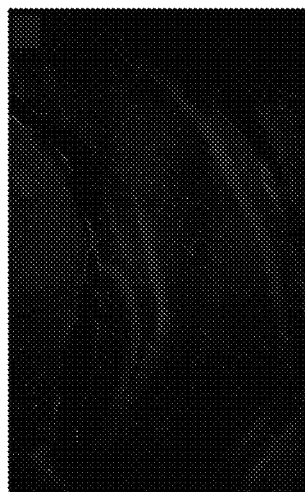
Figure 7C:
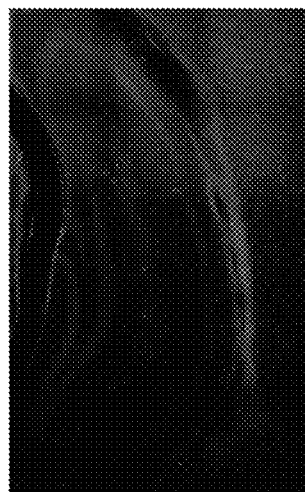
Figure 7D:
Figure 7E:
Figure 7F:
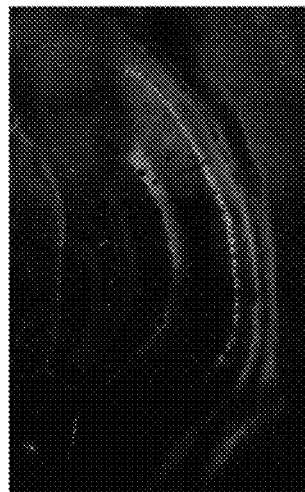

Qualitative Analysis of Neuroprotective Properties in the Pilocarpine-Induced (PILO) Status Epilepticus PILO-induced SE (300 mg/kg) caused strong neurodegenerative changes in the control animals group (FIG. 7A), while in the test group with compound 1 a protective effect was obtained for four mice (B-E), whereas changes were observed for only one mouse (F), as shown in FIG. 7B-F. The obtained results indicate a strong neuroprotective effect of compound 1 in pilocarpine-induced status epilepticus model in mice.

In Vivo Test Results

Effects on Cytochrome P-450 Isoforms CYP3A4, CYP2D6 and CYP2C9

Figure 8A:
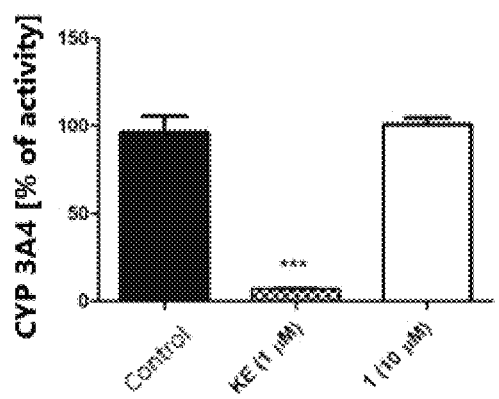
Figure 8B:
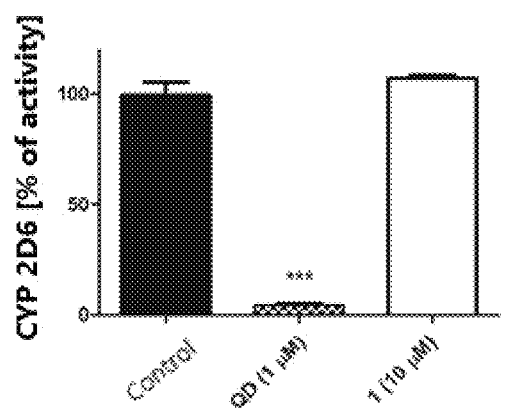
Figure 8C:
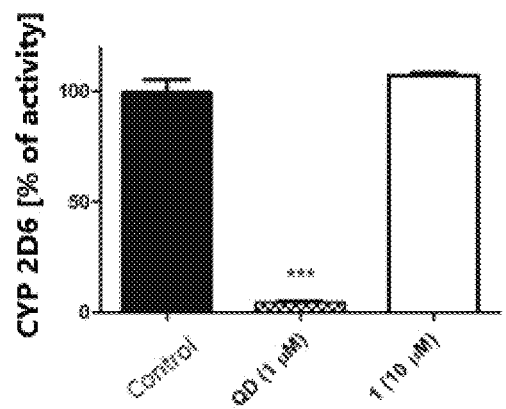

The studies were conducted using commercial luminescence tests CYP3A4 P450-Glo™, CYP2D6 P450-Glo™ and CYP2C9 P450-Glo™ from Promega (Madison, WI, USA). The CYP isoforms selected for study are responsible for the metabolism of approximately 60-70% of the drugs available and their stimulation or inhibition determines the majority of metabolic drug interactions. The results obtained indicate no effect of Compound 1 on CYP3A4 and CYP2D6 activity at a concentration of 10 µM. In contrast, a small, statistically significant ($p<0.05$) inhibition of the CYP2C9 isoform was observed at a high concentration of 10 µM. In summary, the results obtained indicate a low probability of potential metabolic interactions induced by compound 1 (FIG. 8)

Plasma Protein Binding

The distribution parameter of compound 1 was determined by incubating the compound with two major plasma proteins—α1-glycoprotein and human albumin. Then the bound fraction of compound ($f_b$) and the dissociation constant ($K_D$) were calculated, which were $f_b=23.8\%$, $K_D=1970$ µM, respectively. For the reference compound warfarin exhibiting high plasma protein binding, these parameters were $f_b=98.5\%$ and $K_D=9.50$ µM. On the basis of the results obtained, it is shown that low binding of compound 1 to plasma proteins is advantageous, which translates into favorable distribution parameters.

Metabolic Stability

Figure 9:
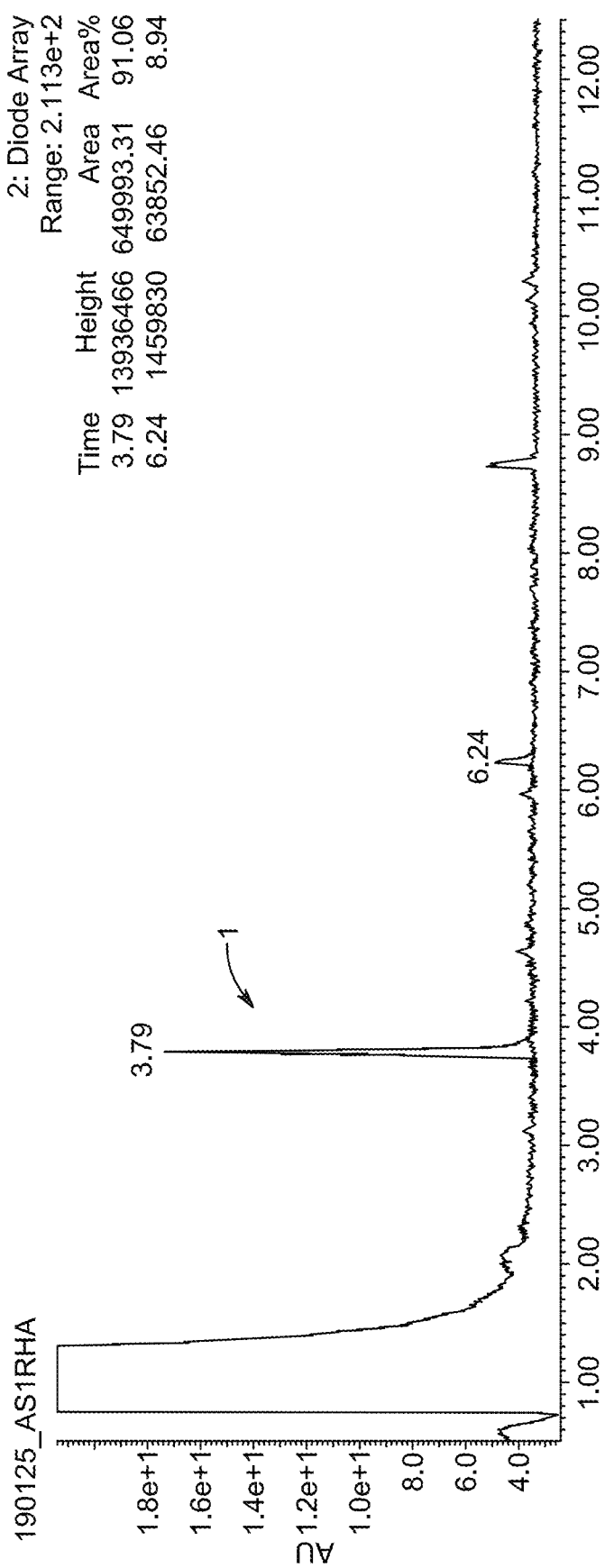
FIG. 9 shows a chromatogram of a reaction mixture after 120 min incubation of compound 1 with human liver microsomes.

Prediction of compound 1 metabolism in the human body was carried out by incubating this compound for 120 minutes with human liver microsomes in the presence of the NADPH cofactor. Based on the resulting UPLC chromatogram of the reaction mixture, no metabolites appeared (FIG. 9). This suggests a very high stability of this compound and resistance to any metabolic transformations by human liver enzymes.

Evaluation of Cytotoxic Activity Against the HaCaT Cell Line in the MTT Test

The cytotoxic activity of compound 1 was estimated by determining the half-maximal inhibitory concentration $IC_{50}$ (concentration of compound that corresponds to 50% cell viability compared to control). Doxorubicin, a drug with confirmed cytotoxicity, was used as a reference compound. Independent experiments were carried out three times in triplicate. Test compound 1 showed significantly lower toxicity compared to doxorubicin, which confirms its very low cytotoxic potential (Table 5).

TABLE 5

Cytotoxic activity (IC$_{50}$, µM) of test compounds in the MTT test.

| Compound | IC$_{50}$ [µM] HaCaT cells* |
|---|---|
| 1 | 239.8 ± 0.6 |
| Doxorubicin | 0.23 ± 0.03 |

*Data are expressed as mean ± SD;
IC$_{50}$ (µM)—compound concentration that corresponds to 50% inhibition of cell line growth (compared to control) after incubating the cells for 72 hours with the individual compound;
Human immortalized keratinocyte cell line (HaCaT);
Doxorubicin—a reference drug exhibiting cytotoxic effect, commonly used in the treatment of cancer.

Evaluation of Cytotoxic Activity Against the HEK-293 Cell Line in the MTS Test

Figure 10:
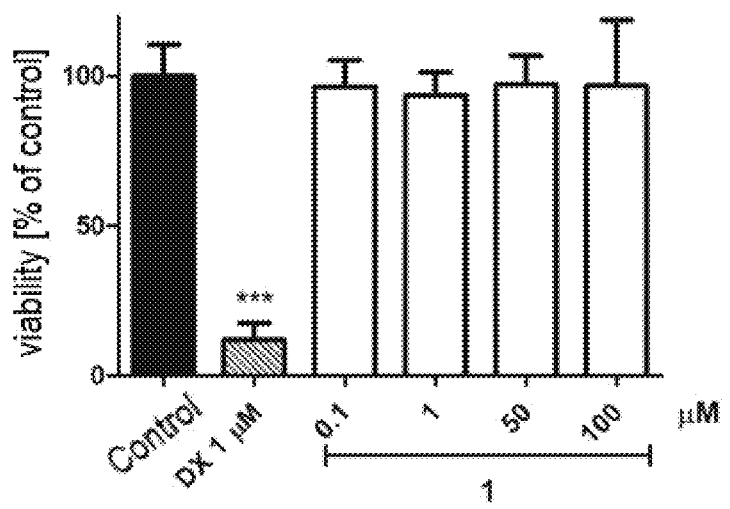
FIG. 10 shows the effect of the reference cytostatics doxorubicin (DX) and compound 1 on HEK-293 cell viability after 72 hours of incubation. Statistical significance was calculated by one-way analysis of variance (ANOVA) and the Bonferroni method (***p<0.001, compounds tested in four replications).

The safety of compound 1 was also assessed using a human embryonic kidney cell line (HEK-293). The MTS colorimetric assay from Promega (Madison, Wis., USA) was used to test the effect of compound 1 on cell viability and proliferation. The compound was tested at four concentrations in the range of 0.1-100 µM. Doxorubicin at a concentration of 1 µM was used as a reference cytostatics. MTS analysis performed after 72 hours of incubation of the HEK-293 line with compound 1 did not show a statistically significant effect of this compound on cell viability in the concentration range of 1-100 µM (FIG. 10).

Assessment of Hepatotoxicity on the HepG2 Cell Line

Figure 11:
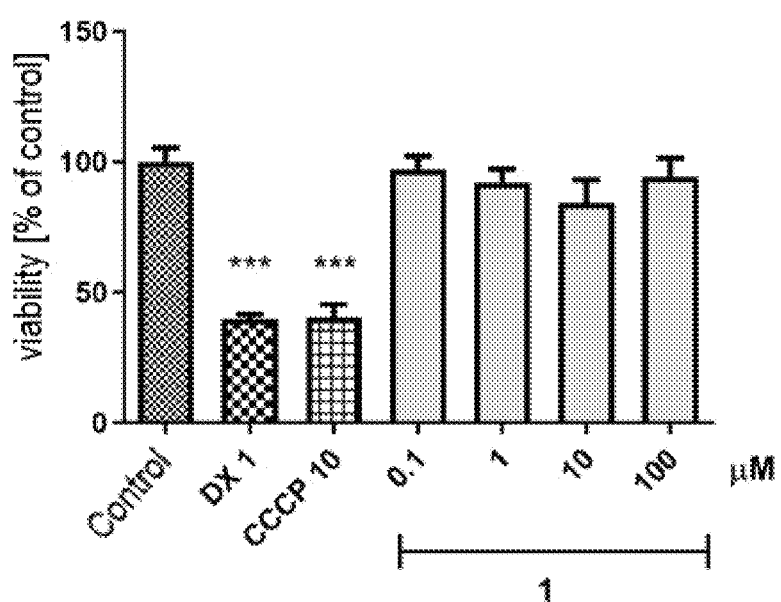
FIG. 11 shows the effect of the reference cytostatics—doxorubicin (DX), mitochondrial toxin CCCP and 1 on HepG2 cell viability after 72 hours of incubation. Statistical significance was calculated by one-way analysis of variance (ANOVA) and the Bonferroni method (***p<0.001, compounds tested in four replications).

Hepatotoxicity of compound 1 was tested using the same procedure as for the toxicity assessment against the HEK-293 line. HepG2 human hepatoma cell line and the CCCP mitochondrial respiratory toxin as reference compound were used in the test. MTS analysis performed after 72 hours of incubation of the HepG2 line with compound 1 did not show a statistically significant effect of this compound on cell viability in the concentration range of 1-100 µM (FIG. 11).

Assessment of Neurotrophic Properties of Compounds 1 and 2 Against Human Neuron Cultures—MTT Test Compounds 1 and 2 in the whole range of concentrations analyzed (from 0.1 to 100 µg/ml) did not affect the viability of human neurons under standard conditions. Removal of trophic factor B27 (trophic stress) from the culture medium reduced the viability of neurons by an average of 15%. Compound 1 at concentrations from 1µg/ml, and compound 2 at concentrations from 0.1 µg/ml acted trophically on nerve cells—eliminating the negative effect of the lack of B27 supplement in culture medium (FIG. 12). The observed effect indicates the in vitro neuroprotective effect of the analyzed compounds.

The invention claimed is:

1. A method of treating a neurological disorder, wherein the method comprises administering to an animal a compound of formula (I):

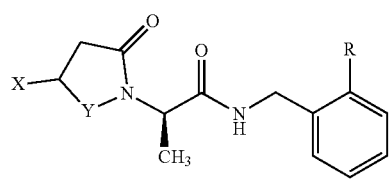

(I)

wherein:
X is hydrogen or N(CH$_3$)$_2$,
Y is CH$_2$ or C=O,
R is hydrogen or halogen,
or a pharmaceutically acceptable salt thereof.

2. The method of claim 1, wherein the animal is a human.

3. The method of claim 2, wherein the human is a child.

4. The method of claim 1, wherein the neurological disorder is selected from the group consisting of epilepsy, epilepsy with concomitant depression and anxiety disorder, neurological pain, neuropathic pain, and a neurodegenerative disease.

5. The method of claim 4, wherein the neurodegenerative disease is Parkinson's disease or Alzheimer's disease or amyotrophic lateral sclerosis.

6. The method of claim 4, wherein the neurological disorder is epilepsy or epilepsy with concomitant depression and anxiety disorder.

7. The method of claim 1, wherein administering the compound of formula (I) does not cause a sedative effect in the animal.

8. The method of claim 1, wherein R in the compound of Formula (I) is F.

9. The method of claim 1, wherein R in the compound of formula (I) is hydrogen.

10. The method of claim 1, wherein the compound of formula (I) is (2R)—N-benzyl-2-(2,5-dioxopyrrolidin-1-yl)propanamide.

11. The method of claim 1, wherein the compound of formula (I) is (2R)-2-(2,5-dioxopyrrolidin-1-yl)—N-(2-fluorobenzyl)propanamide.

12. The method of claim 1, wherein the compound of formula (I) is (2R)—N-benzyl-2-(2-oxopyrrolidin-1-yl)propanamide.

13. The method of claim 1, wherein the compound of formula (I) is (2R)—N-(2-fluorobenzyl)-2-(2-oxopyrrolidin-1-yl)propanamide.

14. The method of claim 1, wherein the compound of formula (I) is (2R)—N-benzyl-2-(3-(dimethylamino)-2,5-dioxopyrrolidin-1-yl)propanamide.

15. The method of claim 1, wherein the compound of formula (I) is (2R)-2-(3-(dimethylamino)-2,5-dioxo-pyrrolidin-1-yl)—N-(2-fluorobenzyl)propanamide.

16. A method of treating a psychiatric disorder, wherein the method comprises administering to an animal a compound of formula (I):

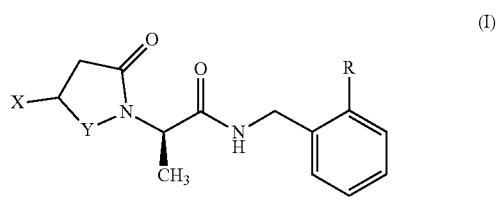

(I)

wherein:
X is hydrogen or N (CH$_3$)$_2$,
Y is CH$_2$ or C=O,
R is hydrogen or halogen,
or a pharmaceutically acceptable salt thereof.

17. The method of claim 16, wherein the psychiatric disorder is depression, anxiety, or depression and anxiety.

18. The method of claim 16, wherein the animal is a human.

19. The method of claim 16, wherein R in the compound of formula (I) is F.

20. The method of claim 16, wherein R in the compound of formula (I) is hydrogen.

21. The method of claim 16, wherein the compound of formula (I) is (2R)—N-benzyl-2-(2,5-dioxopyrrolidin-1-yl)propanamide.

22. The method of claim 16, wherein the compound of formula (I) is (2R)-2-(2,5-dioxopyrrolidin-1-yl)—N-(2-fluorobenzyl)propanamide.

23. The method of claim 16, wherein the compound of formula (I) is (2R)—N-benzyl-2-(2-oxopyrrolidin-1-yl)propanamide.

24. The method of claim 16, wherein the compound of formula (I) is (2R)—N-(2-fluorobenzyl)-2-(2-oxopyrrolidin-1-yl)propanamide.

25. The method of claim 16, wherein the compound of formula (I) is (2R)—N-benzyl-2-(3-(dimethylamino)-2,5-dioxopyrrolidin-1-yl)propanamide.

26. The method of claim 16, wherein the compound of formula (I) is (2R)-2-(3-(dimethylamino)-2,5-dioxo-pyrrolidin-1-yl)—N-(2-fluorobenzyl)propanamide.

27. A method of treating inflammatory pain, wherein the method comprises administering to an animal a compound of formula (I):

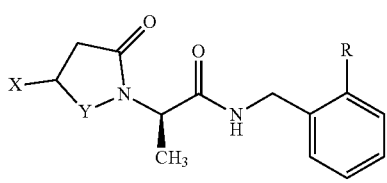

wherein:
X is hydrogen or N(CH$_3$)$_2$,
Y is CH$_2$ or C=O,
R is hydrogen or halogen,
or a pharmaceutically acceptable salt thereof.

28. A method of preventing seizures, reducing the frequency of seizures, or reducing the severity of seizures, wherein the method comprises administering to an animal a compound of formula (I):

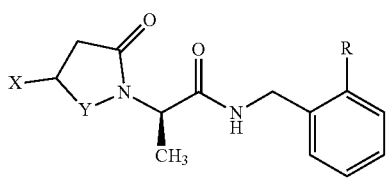

or a pharmaceutically acceptable salt thereof, wherein:
X is hydrogen or N(CH$_3$)$_2$;
Y is CH$_2$ or C=O; and
R is hydrogen or halogen.

29. The method of claim 28, wherein the method is a method of preventing seizures.

30. The method of claim 28, wherein the method is a method of reducing the frequency of seizures.

31. The method of claim 28, wherein the method is a method of reducing the severity of seizures.

32. The method of claim 28, wherein the animal is a human.

33. The method of claim 29, wherein the human is a child.

34. The method of claim 28, wherein the compound of formula (I) is (2R)—N-benzyl-2-(2,5-dioxopyrrolidin-1-yl)propanamide.

35. The method of claim 28, wherein the compound of formula (I) is (2R)-2-(2,5-dioxopyrrolidin-1-yl)—N-(2-fluorobenzyl)propanamide.

36. The method of claim 28, wherein the compound of formula (I) is (2R)—N-benzyl-2-(2-oxopyrrolidin-1-yl)propanamide.

37. The method of claim 28, wherein the compound of formula (I) is (2R)—N-(2-fluorobenzyl)-2-(2-oxopyrrolidin-1-yl)propanamide.

38. The method of claim 28, wherein the compound of formula (I) is (2R)—N-benzyl-2-(3-(dimethylamino)-2,5-dioxopyrrolidin-1-yl)propanamide.

39. The method of claim 28, wherein the compound of formula (I) is (2R)-2-(3-(dimethylamino)-2,5-dioxo-pyrrolidin-1-yl)—N-(2-fluorobenzyl)propanamide.

40. The method of claim 28, wherein administering the compound of formula (I) does not cause a sedative effect in the animal.

41. The method of claim 28, wherein the seizure is a drug-resistant seizure.

42. The method of claim 27, wherein R in the compound of Formula (I) is F.

43. The method of claim 27, wherein R in the compound of formula (I) is hydrogen.

44. The method of claim 27, wherein the compound of formula (I) is (2R)-N-benzyl-2-(2,5-dioxopyrrolidin-1-yl)propanamide.

45. The method of claim 27, wherein the compound of formula (I) is (2R)-2-(2,5-dioxopyrrolidin-1-yl)-N-(2-fluorobenzyl) propanamide.

46. The method of claim 27, wherein the compound of formula (I) is (2R)-N-benzyl-2-(2-oxopyrrolidin-1-yl) propanamide.

47. The method of claim 27, wherein the compound of formula (I) is (2R)-N-(2-fluorobenzyl)-2-(2-oxopyrrolidin-1-yl) propanamide.

48. The method of claim 27, wherein the compound of formula (I) is (2R)-N-benzyl-2-(3-(dimethylamino)-2,5-dioxopyrrolidin-1-yl) propanamide.

49. The method of claim 27, wherein the compound of formula (I) is (2R)-2-(3-(dimethylamino)-2,5-dioxo-pyrrolidin-1-yl)-N-(2-fluorobenzyl) propanamide.

50. The method of claim 28, wherein R in the compound of Formula (I) is F.

51. The method of claim 28, wherein R in the compound of formula (I) is hydrogen.

* * * * *